United States Patent
Dadachova et al.

(10) Patent No.: US 7,651,689 B2
(45) Date of Patent: Jan. 26, 2010

(54) METHODS OF APPLYING IONIZATION RADIATION FOR THERAPY OF INFECTIONS

(75) Inventors: Ekaterina Dadachova, Mahopac, NY (US); Arturo Casadevall, Pelham, NY (US); Antonio Nakouzi, Bayside, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 10/704,469

(22) Filed: Nov. 7, 2003

(65) Prior Publication Data

US 2004/0115203 A1    Jun. 17, 2004

Related U.S. Application Data

(60) Provisional application No. 60/426,566, filed on Nov. 15, 2002.

(51) Int. Cl.
    *A61K 39/395* (2006.01)
(52) U.S. Cl. ............... 424/152.1; 424/181.1; 424/178.1
(58) Field of Classification Search ................ 424/1.49, 424/1.69, 1.53, 152.1, 141.1, 1.11; 530/350, 530/391.1, 388.73, 391.3, 388.15, 402; 435/320.1, 435/69.1
See application file for complete search history.

(56) References Cited

U.S. PATENT DOCUMENTS

| | | | |
|---|---|---|---|
| 4,444,744 A * | 4/1984 | Goldenberg | 424/1.49 |
| 4,636,380 A * | 1/1987 | Wong | 424/1.53 |
| 4,925,648 A * | 5/1990 | Hansen et al. | 424/1.53 |
| 4,937,183 A * | 6/1990 | Ultee et al. | 424/1.53 |
| 5,102,990 A * | 4/1992 | Rhodes | 424/1.49 |
| 5,128,119 A * | 7/1992 | Griffiths | 424/1.49 |
| 5,288,639 A * | 2/1994 | Burnie et al. | 435/320.1 |
| 5,332,567 A * | 7/1994 | Goldenberg | 424/1.49 |
| RE35,152 E * | 2/1996 | Rubin | 128/654 |
| 5,541,077 A * | 7/1996 | Burnie et al. | 435/7.31 |
| 5,541,297 A | 7/1996 | Hansen et al. | |
| 5,601,825 A | 2/1997 | Hansen et al. | |
| 5,677,427 A | 10/1997 | Goldenberg et al. | |
| 5,686,248 A * | 11/1997 | Burnie et al. | 435/6 |
| 5,705,158 A * | 1/1998 | Hansen et al. | 424/181.1 |
| 5,733,572 A * | 3/1998 | Unger et al. | 424/450 |
| 5,770,222 A * | 6/1998 | Unger et al. | 424/450 |
| 5,811,236 A * | 9/1998 | Massey et al. | 435/6 |

(Continued)

OTHER PUBLICATIONS

Casadevall, A. et al, Antimicrobial Agents and Chemotherapy, vol. 42(6), pp. 1437-1446, Jun. 1998, Characterization of a murine monoclonal antibody to *Cryptococcus neoformans* polysaccharide that is a candidate for human therapeutic studies.*

(Continued)

*Primary Examiner*—Robert B Mondesi
*Assistant Examiner*—Ginny Portner
(74) *Attorney, Agent, or Firm*—Amster, Rothstein & Ebenstein LLP

(57) ABSTRACT

This invention provides methods for treating infections in a subject which comprise administering to the subject an amount of a radiolabeled antibody effective to treat the infection, wherein the antibody specifically binds to the agent causing the infection. The invention also provides compositions and methods of making compositions comprising radiolabeled antibodies for the treatment of infections.

19 Claims, 14 Drawing Sheets

A)

B)

U.S. PATENT DOCUMENTS

| | | | | |
|---|---|---|---|---|
| 5,840,272 | A | * | 11/1998 | Subramanian ............. 424/1.49 |
| 5,874,104 | A | * | 2/1999 | Adler-Moore et al. ...... 424/450 |
| 6,077,499 | A | | 6/2000 | Griffiths |
| 6,319,500 | B1 | * | 11/2001 | Goldenberg ............. 424/178.1 |
| 6,409,990 | B1 | * | 6/2002 | Vera ......................... 424/9.35 |
| 6,458,933 | B1 | * | 10/2002 | Hansen ................... 530/387.3 |
| 6,509,325 | B1 | * | 1/2003 | Nosanchuk et al. ......... 514/109 |
| 6,548,275 | B2 | * | 4/2003 | Goldenberg ............... 435/69.7 |
| 6,653,104 | B2 | | 11/2003 | Goldenberg |
| 6,667,024 | B1 | | 12/2003 | Goldenberg et al. |
| 6,720,152 | B1 | * | 4/2004 | Weil et al. .................... 435/7.1 |
| 6,962,702 | B2 | | 11/2005 | Hansen et al. |
| 7,402,385 | B2 | * | 7/2008 | Dadachova et al. ............ 435/6 |
| 2001/0055595 | A1 | * | 12/2001 | Goldenberg ............. 424/178.1 |
| 2002/0006379 | A1 | * | 1/2002 | Hansen et al. ............. 424/1.49 |
| 2002/0136690 | A1 | * | 9/2002 | Goldenberg ............... 424/1.49 |
| 2002/0168748 | A1 | * | 11/2002 | Berlin et al. ................ 435/199 |
| 2002/0187141 | A1 | * | 12/2002 | Goldenberg ............. 424/130.1 |
| 2003/0103977 | A1 | * | 6/2003 | Casadevall et al. ........ 424/151.1 |
| 2003/0124184 | A1 | * | 7/2003 | Edwards et al. ........... 424/184.1 |
| 2003/0170697 | A1 | * | 9/2003 | Goldenberg .................... 435/6 |
| 2003/0180285 | A1 | * | 9/2003 | Burnie .................... 424/130.1 |
| 2003/0198595 | A1 | * | 10/2003 | Goldenberg et al. ........ 424/1.49 |
| 2003/0232010 | A2 | * | 12/2003 | Goldenberg ............... 424/1.49 |
| 2004/0043030 | A1 | * | 3/2004 | Griffiths et al. ........... 424/178.1 |
| 2004/0071692 | A1 | * | 4/2004 | Goldenberg ............. 424/130.1 |
| 2004/0156780 | A1 | * | 8/2004 | Dadachova et al. ......... 424/1.49 |
| 2004/0170620 | A1 | * | 9/2004 | Thorpe et al. ............. 424/130.1 |
| 2004/0213791 | A1 | * | 10/2004 | Bander et al. ............. 424/155.1 |
| 2005/0002945 | A1 | * | 1/2005 | McBride et al. ........... 424/184.1 |
| 2005/0112708 | A1 | * | 5/2005 | Prince et al. ............... 435/7.31 |
| 2005/0187161 | A1 | * | 8/2005 | Kontoyiannis et al. ......... 514/14 |
| 2006/0193865 | A1 | * | 8/2006 | Govindan ................ 424/155.1 |
| 2006/0228300 | A1 | * | 10/2006 | Chang et al. ............... 424/1.49 |

OTHER PUBLICATIONS

Zebedee, SL et al, Antimicrobial Agents and Chemotherapy, vol. 38(7), pp. 1507-1514, Jul. 1994, Mouse-Human Immunoglobulin G1 chimeric antibodies with activities against *Cryptococcus neoformans*.*

Schaefer, DA et al, Infection and Immunity, vol. 68(3), pp. 2608-2616, May 2000, Characterization and Formulation of multiple epitope specific neutralizing monoclonal antibodies for passive immunization against *Cryptosporidiosis*.*

Rosas, AL et al, Infection and Immunity, vol. 69(5), pp. 3410-3412, May 2001 Passive immunization with melanin-binding monoclonal antibodies prolongs survival of mice with lethal *Cryptococcus neoformans* infection.*

Goldman, DL et al, Journal of Med. Vet. Mycol. 1997, Jul.-Aug, 35(4), p. 271-278, Pharmacokinetics and biodistribution of a mab antibody to *C neoformans* capsular polysaccharide antigen in a rat model of cryptococcal meningits:implications.*

Dadachova et al, abstract UL-22, Dec. 16-19, 2001 ICAAC Abstracts Addendum, Chicago 2001, American Society of Microbiology.*

Goldenberg, DN et al, J. Nuclear Medicine, vol. 35(6), pp. 1028-1034 1994 (abstract only).*

Casadevall, A, 1998, Exp. Opin. Invest. Drugs, vol. 7(3), pp. 307-321.*

Crudo, JL et al, International Journal of Pharmaceutics, vol. 248, pp. 173-182, Nov. 6, 2002.* van Gog, FB et al, J. Nuclear Medicine, vol. 37(2), Feb. 1996, pp. 352-362.*

Gross, NT et al, Letters in Applied Microbiology, 2000, pp. 218-222, Treatment of experimental *Cryptococcus neoformans* infecton in newborn rabbits by airwy installation of specific antibody and surfactant.*

Steenbergan, JN et al, PNAS, Dec. 18, 2001, vol. 98(26), pp. 15245-15250.*

Toledo, Marcos S et al, Glycobiology, vol. 11(2), pp. 105-112, 2001.*

Dadachova, E et al, The Quarterly Journal of Neuclear Medicine and Molecular imaging, vol. 50, pp. 193-204, 2006.*

Dromer et al, 1987, reference of record.*

Goldman et al, J. Med. Vet. Mycology, 1997, Jul.-Aug. vol. 35(4), pp. 271-278 (abstract only).*

Casadevall, A et al, Antimicrobial Agents and Chemotherapy, Jun. 1998, pp. 1437-1446, vol. 42(6).*

Dromer et al, 1987, Infection and Immunity, vol. 55, pp. 749-752.*

Mukherjee et al, 1992, Infection and Immunity, vol. 60, pp. 4534-4561.*

Yuan, R et al, 1998, J. Exp. Med., vol. 187, pp. 641-648.*

Dadachova E et al., entitled "Ionizing radiation delivered by specific antibody is therapeutic against a fungal infection," Proc Natl Acad Sci USA, Sep. 16, 2003;100(19):10942-7.

Dadachova E et al., entitled "Radioimmunotherapy with radiolabeled organism-specific antibody is effective against opportunistic fungal pathogen," 9th Conference on Cancer Therapy with Antibodies & Immunoconjugates, P-09, 2002, Abstract.

Dadachova E et al., entitled "Radioimmunotherapy of *C.neoformans* infection in vivo," J. Nucl. Med., 43 (5) Suppl., p. 83 (2002), Abstract.

Dadachova E et al., entitled "Treatment of Infection with Ionizing Radiation In Vivo," 41st Interscience Conference on Antimicrobial Agents and Chemotherapy, Abstracts Addendum, Dec. 16-19, 2001, p. 8.

Dadachova E et al., entitled "Radioimmunotherapy of fungal infection with 213-Bi- and 188-Re-labeled antibody," World Journal of Nuclear Medicine, vol. 1, Suppl. 2, Sep. 2002, S58, Abstract.

Dadachova E et al., entitled Radioimmunotherapy of infections using alpha- and beta-emitting radionuclides, 225th American Chemical Society Meeting, Division of Nuclear Chemistry and Technology, Abs. #82 (2003).

Bryan R A et al., entitled Targeted in vitro and in vivo killing of *Cryptococcus neoformans* by radioactively labeled antibodies. American Society for Microbiology 103rd General Meeting, Abstract F-100 (2003).

Ramachandran R V et al., entitled "Failure of short-term CD4-PE40 infusions to reduce virus load in human immunodeficinecy virus-infected persons," J Infect Dis., Oct. 1994;170(4):1009-13, Abstract Only.

Davey R T Jr. et al., entitled "Use of recombinant soluble CD4 *Psuedomonas exotoxin*, a novel immunotoxin, for treatment of persons infected with human immunodeficiency virus," J Infect Dis., Nov. 1994;170(5):1180-8, Abstract Only.

Vitetta E S, entitled "Immunotoxins: New Therapeutic Reagents for Autoimmunity, Cancer, and AIDS," Journal of Clinical Immunology, vol. 10, No. 6 (Nov. Supplement 1990), 15S-18S.

US 6,558,648, 05/2003, Griffiths et al. (withdrawn)

* cited by examiner

A)

B)

A)

B)

US 7,651,689 B2

METHODS OF APPLYING IONIZATION RADIATION FOR THERAPY OF INFECTIONS

PRIORITY CLAIM

This application claims the benefit of U.S. Provisional Application No. 60/426,566, filed Nov. 15, 2002, the content of which is hereby incorporated by reference in its entirety into the subject application.

STATEMENT OF GOVERNMENT SUPPORT

The invention disclosed herein was made with U.S. Government support under grant numbers AI33774, AI13342, AI52042, and HL59842 from the National Institutes of Health, U.S. Department of Health and Human Services. Accordingly, the U.S. Government has certain rights in this invention.

FIELD OF THE INVENTION

The present invention relates to the treatment of infections, particularly intractable infections, such as fungal infections in immunosuppressed subjects, using radioimmunotherapy.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

The field of infectious diseases is currently in crisis given that: 1) there is an increasing prevalence of infections with highly resistant microorganisms that are not susceptible to existing antimicrobial agents; 2) many infections occur in immunosuppressed individuals in whom standard antimicrobial therapy is not very effective; and 3) there is a dearth of new anti-microbials drugs in the development pipeline as evidenced by the paucity of new drugs in the past decade. In this environment new approaches are needed to antimicrobial therapy in general and to AIDS-associated opportunistic infections therapy in particular.

Fungal diseases in particular are notoriously difficult to treat and currently constitute a major clinical problem in immunosuppressed patients (e.g., HIV-infected individuals, cancer patients, organ transplant recipients) because antifungal drugs do not eradicate the infection in the setting of severe immune dysfunction (7-9). Most life-threatening invasive fungal infections occur in severely immunosuppressed individuals (7).

*Cryptococcus neoformans* (CN) is a major fungal pathogen that causes life-threatening meningoencephalitis in 6-8% of patients with AIDS. Cryptococcal infections in immunosuppressed patients are often incurable (8,9). Immunotherapy of CN infection with passive antibody is being evaluated (10). However, with passive antibody treatment, a loss of effectiveness can occur when the antibody is administered in amounts greater than an optimally protective amount (45). Another fungal species, *Histoplasma capsulatum* (HC) is the most common causes of fungal pneumonia (60).

Another example of an important pathogen is *Streptococcus pneumoniae*, which is an important cause of community-acquired pneumonia, meningitis, and bacteremia. The problem of pneumococcal disease is increased by drug resistance (73). Furthermore, there is an increased prevalence of invasive pneumococcal infections in patients with immune impairment caused by chemotherapy or immune suppression in the setting of organ transplantation or HIV infection (74). Thus, there is an urgent need for new approaches to antipneumococcal therapy.

Furthermore, the $21^{st}$ century has witnessed a global outbreak of SARS and the introduction of monkey pox virus into the United States. In this environment, new approaches to antimicrobial therapy are needed. Specifically new strategies are required that can translate into the rapid development of new antimicrobial agents. Current strategies for the development of antimicrobial drugs and vaccines take many years to yield clinically useful products.

Radioimmunotherapy (RIT) is a therapeutic modality which uses antibody-antigen interaction and utilizes antibodies radiolabeled with therapeutic radioisotopes to deliver lethal doses of radiation to cells in cancer treatment (40). Radiolabeled antibodies provide valuable alternatives to cancer treatment with chemotherapy or external radiation beam by selectively delivering lethal doses of radiation to cancerous cells. There is an abundance of published information on the interaction of radiolabeled antibodies with target cancer cells, surrounding tissue and major organs obtained from laboratory and clinical studies (41-43). Radioisotopes with decay characteristics allowing treatment of relatively large lesions (up to several cm in diameter), or, on the contrary, single cell disease, are now available. Although RIT of cancer has been studied for almost 20 years, during this time there has been no attempt to apply RIT to the field of infectious diseases.

Radiation also possesses microbicidal properties and γ-irradiation is routinely used for sterilization of medical supplies and certain foods. Ionizing radiation such as γ-rays, β- and especially α-particles from external sources can kill different strains of bacteria and fungi such as *E. coli, M tuberculosis*, and *C. neoformans* (1-3). However, many fungi manifest extreme radioresistance to external gamma radiation relative to other microorganisms and mammalian cells (1, 2, 55, 56, 58). For example, a dose of several thousands Gy is required to achieve 90% cell killing of fungal cells whereas the lethal dose for mammalian cells in only a few Gy. The mechanisms responsible for these differences are not well understood but could involve more efficient mechanisms of DNA repair by fungi when the damage is caused by gamma rays. A dramatic example of the radioresistance of fungi is provided by reports of numerous melanotic fungal species colonizing the walls of the damaged nuclear reactor at Chernobyl in extremely high radiation fields (59).

In order to realize the full benefits of ionizing radiation as an anti-infective treatment, it is important to target the radiation to the sites of infection to minimize toxicity to the host. In contrast to tumor cells, infectious agents such as fungal and bacterial cells are antigenically very different from host tissue and thus provide the potential for abundant pathogen-antibody interactions with low cross-reaction with tissue. In this regard, pathogen-specific antibodies have been used experimentally for the diagnosis of certain infectious diseases, as exemplified by the application of $^{99m}$Tc-Fab' fragments directed against *Pneumocystis carinii* to visualize the site of infection in patients (5) and by the visualization of tuberculomas in a rabbit model with an antibody to *M. bovis* (BCG) (6). The successful detection of infection with radiolabeled antibodies indicates that antigen-antibody interactions can be used to deliver radionuclides to microorganisms in vivo. However, since certain types of microorganisms (e.g., bacterium *Deinococcus radiodurans*, and yeasts *Cryptococcus*

*neoformans, Saccharomyces ellipsoideus* and *Saccharomyces cerevisiae*) are extremely resistant to gamma radiation (2, 54-56), it has not been apparent whether infectious microorganisms are susceptible to particulate radiation.

SUMMARY OF THE INVENTION

The present invention is directed to the combination of immune and radiation therapy for the treatment of infections, particularly intractable infections such as fungal infections. The radioimmunotherapy (RIT) approach is expected to be of particular value in cases which include the following: 1) treatment of infections in special populations such as immunosuppressed patients infected with *C. neoformans* or with other AIDS-associated opportunistic infections; 2) treatment of infections, particularly fungal infections, in immunosuppressed cancer patients or organ transplant recipients; 3) multi-drug resistant infections, since the antibody-antigen interaction is not subject to a multi-drug resistance mechanism; 4) infections for which there is no known treatment; and 5) treatment of high-risk patients with latent infections since RIT does not have the adverse side effects of chemotherapy with antibiotics.

The subject invention is directed to a method for treating an infection in a subject which comprises administering to the subject an amount of a radiolabeled antibody effective to treat the infection, wherein the antibody specifically binds to an agent causing the infection. The invention is further directed to a method for treating an infection in a subject which comprises administering to the subject an amount of antibodies radiolabeled with a plurality of different radioisotopes effective to treat the infection, wherein the antibodies specifically bind to an agent causing the infection.

The invention provides a method of making a composition effective to treat an infection in a subject which comprises admixing a radiolabeled antibody and a carrier, wherein the antibody specifically binds to an agent causing the infection. The invention provides a composition comprising an amount of a radiolabeled antibody effective to treat an infection in a subject and a carrier, wherein the antibody specifically binds to an agent causing the infection.

DETAILED DESCRIPTION OF THE INVENTION

Figure 1A:
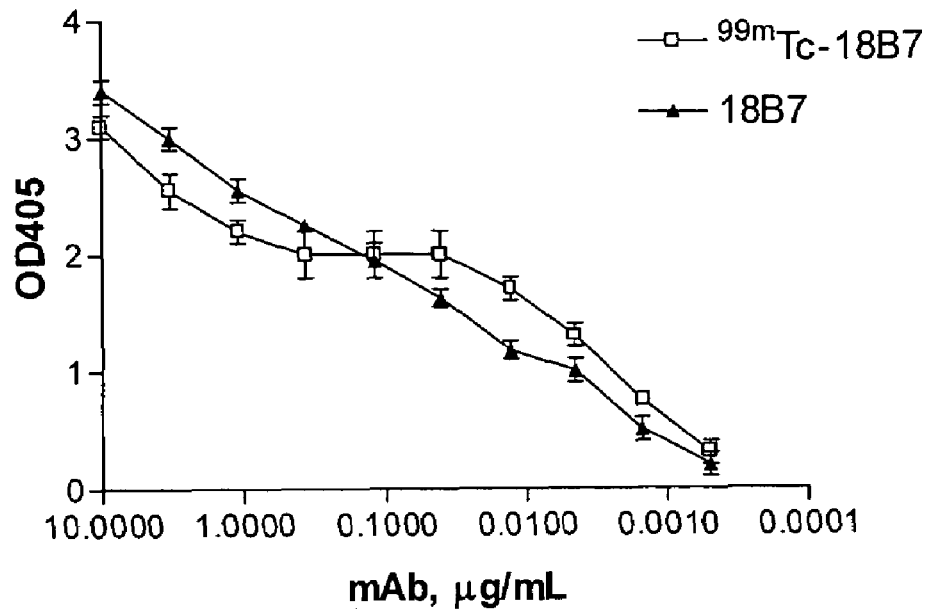
FIGS. 1A-1B. Immunoreactivity of radiolabeled 18B7 antibody by ELISA: A) $^{99m}$Tc-18B7; B) $^{111}$In—CHXA"-18B7. Initial 1.5 molar excess of CHXA" ligand over 18B7 antibody in conjugation reaction resulted in attachment of 0.8 CHXA" per 18B7 molecule. Experiments were done in triplicate.

The subject invention is directed to a method for treating an infection in a subject which comprises administering to the subject an amount of a radiolabeled antibody effective to treat the infection, wherein the antibody specifically binds to an agent causing the infection. The invention is further directed to a method for treating an infection in a subject which comprises administering to the subject an amount of antibodies radiolabeled with a plurality of different radioisotopes effective to treat the infection, wherein the antibodies specifically bind to an agent causing the infection.

The term "infection" is used to include infections that produce an infectious disease. The infection diseases include communicable diseases and contagious diseases. As used herein, the term "treat" an infection means to eliminate the infection, to reduce the number of the microorganisms causing the infection in the subject, to prevent the infection from spreading in the subject, or to reduce the further spread of the infection in the subject.

In preferred embodiments, the subject is an immunosuppressed subject or a subject in whom the infection is intractable to treatment using conventional methods. Immunosuppression can occur due to inhibition of one or more components of the immune system due to an underlying disease. Immunosuppression can also be intentionally induced by drugs, for example in patients receiving tissue transplants or in patients with autoimmune disease. Examples of immunosuppressed subjects include, but are not limited to, individuals infected with human immunodeficiency virus (HIV), cancer patients, and organ transplant recipients. HIV causes acquired immune deficiency syndrome (AIDS).

The subject can be a mammal. In different embodiments, the mammal is a mouse, a rat, a cat, a dog, a horse, a sheep, a cow, a steer, a bull, livestock, a primate, a monkey, or preferably a human.

As used in the subject application, the term "antibody" encompasses whole antibodies, fragments of whole antibodies wherein the fragments specifically bind to an agent causing an infection, and peptides that specifically bind to an agent causing an infection. The complementarity determining region of an antibody is the region that forms the antigen-binding site. Antibody fragments include, but are not limited to, F(ab')$_2$ and Fab' fragments. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. The term antibody is further meant to encompass polyclonal antibodies and monoclonal antibodies.

The antibody can be any of an IgA, IgD, IgE, IgG, or IgM antibody. The IgA antibody can be an IgA1 or an IgA2 antibody. The IgG antibody can be an IgG1, IgG2, IgG2a, IgG2b, IgG3 or IgG4 antibody. A combination of any of these antibodies subtypes can also be used. One consideration in selecting the type of antibody to be used is the desired serum half-life of the antibody. IgG has a serum half-life of 23 days, IgA 6 days, IgM 5 days, IgD 3 days, and IgE 2 days (78). Another consideration is the size of the antibody. For example, the size of IgG is smaller than that of IgM allowing for greater penetration of IgG into tissues. IgA, IgG, and IgM are preferred antibodies.

In a preferred embodiment, the infection is a fungal infection. Examples of fungal infections include, but are not limited to, infections due to *Cryptococcus neoforman, Histoplasma capsulatum* or *Aspergillus fumigatus*. In one embodiment, the fungus is *Cryptococcus neoforman*, and the subject is infected with HIV. In one embodiment, the fungus is *Aspergillus fumigatus*, and the subject is an organ transplant patient.

In a prefered embodiment, the antibody is 18B7, which binds to *Cryptococcus neoforman*. In other embodiments, the antibody is 6D2 (52), which binds to melanin-pigmented fungal pathogens such as *Histoplasma capsulatum* and *Aspergillus fumigatus*. In a preferred embodiment, the fungus is *Histoplasma capsulatum* and the antibody is 9C7. Prefered antibodies are IgG1 antibodies and IgM antibodies.

Preferably, the radiation dose that is effective to kill the fungus is at least 100 fold less than the dose of external gamma radiation that is effective to kill the fungus. The radiation dose that is effective to kill the fungus can be two orders of magnitude less than the dose of external gamma radiation that is effective to kill the fungus. More preferably, the radiation dose that is effective to kill the fungus is three orders of magnitude less than the dose of external gamma radiation that is effective to kill the fungus.

The choice of the particular radioisotope with which the antibody is labeled will be determined by the type of infection to be treated and its localization in the body. Two characteristics are important in the choice of a radioisotope-emission range in the tissue and half-life. Alpha emitters, which have a short emission range in comparison to beta emitters, may be preferable for treatment of infections that are disseminated in the body. Examples of alpha emitters include 213-Bismuth (half-life 46 minutes), 223-Radium (half-life 11.3 days), 224-Radium (half-life 3.7 days), 225-Radium (half-life 14.8 days), 225-Actinium (half-life 10 days), 212-Lead (half-life 10.6 hours), 212-Bismuth (half-life 60 minutes), 211-Astatin (half-life 7.2 hours), and 255-Fermium (half-life 20 hours). In a preferred embodiment, the alpha-emitting radioisotope is 213-Bismuth. $^{213}$Bi emits a high LET α-particle with E=5.9 MeV with a path length in tissue of 50-80 µm. Theoretically a cell can be killed with one or two α-particle hits. $^{213}$Bi is the only α-emitter that is currently available in generator form, which allows transportation of this isotope from the source to clinical centers within the United States and abroad.

Beta emitters, with their longer emission range, may be preferable for the treatment of abscesses. Examples of beta emitters include 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131-Iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199-Gold (half-life 3.1 days). In a preferred embodiment, the beta-emitting radioisotope is the high-energy β-emitter 188-Rhenium ($E_{max}$=2.12 MeV). $^{188}$Re has the additional advantage that it emits γ-rays which can be used for imaging studies. For the treatment of infections within large abscesses or in difficult to access sites deep in the body, longer-lived isotopes such as 90-Yttrium (half-life 2.7 days), 177-Lutetium (half-life 6.7 days) or 131-Iodine (half-life 8 days) may be preferred. Positron emitters, such as 68-Gallium (half-life 68 minutes), 18-Fluorine (half-life 110 minutes), and 61-Copper (half-life 3.4 hours), could also be used to treat abscesses, as well as disseminated diseases. In addition, radioisotopes which are Auger electron emitters and/or conversion electron emitters could be used for any type of infection; however, such radioisotopes need to be coupled to an antibody which is internalized by the cell to which the antibody binds. Examples of Auger electron emitters include 67-Gallium (half-life 78 hours), 111-Indium (half-life 2.8 days), 123-Iodine (half-life 13 hours), 125-Iodine (half-life 60 days) and 201-Thallium (half life 3 days). Examples of conversion electron emitters include 117m-Tin (half-life 13.6 days). Examples of radioisotopes that emit both Auger electrons and conversion electrons include 195m-Mercury (half-life 41.6 hours) and 195m-Platinum (half-life 4 days).

The radioisotope can be attached to the antibody using any known means of attachment used in the art, including interactions such as avidin-biotin interactions.

In a preferred embodiment, the invention provides a method for treating an infection in a subject which comprises administering to the subject an amount of antibodies radiolabeled with a plurality of different radioisotopes effective to treat the infection, wherein the antibodies specifically bind to an agent causing the infection. Preferably, the radioisotopes are isotopes of a plurality of different elements. In a preferred embodiment, at least one radioisotope in the plurality of different radioisotopes is a long range emitter and at least one radioisotope is a short range emitter. Examples of long range emitters include beta emitters and positron emitters. Examples of short range emitters include alpha emitters, Auger electron emitters, and conversion electron emitters. Positron emitters can also be intermediate range emitters depending on the energy of the positrons. In a preferred embodiment, the long-range emitter is a beta emitter and the short range emitter is an alpha emitter. Preferably, the beta emitter is 188-Rhenium. Preferably, the alpha emitter is 213-Bismuth. Combinations of different radioisotopes can be used, which include an admixture of any of an alpha emitter, a beta emitter, a positron emitter, an Auger electron emitter, and a conversion electron emitter, with physical half-lives from 30 minutes to 100 days. Preferably, the plurality of different radioisotopes is more effective in treating the infection than a single radioisotope within the plurality of different radioisotopes, where the radiation dose of the single radioisotope is the same as the combined radiation dose of the plurality of different radioisotopes. More preferably, the plurality of different radioisotopes is at least four fold more effective in treating the infection than the single radioisotope within the plurality of different radioisotopes.

It is known from radioimmunotherapy studies of tumors that whole antibodies usually require from 1 to 3 days time in circulation to achieve maximum targeting. While slow targeting may not impose a problem for radioisotopes with relatively long half-lives such as $^{188}$Re ($t_{1/2}$=16.7 hours), faster delivery vehicles are needed for short-lived radioisotopes such as $^{213}$Bi ($t_{1/2}$=46 min). The smaller F(ab')$_2$ and Fab' fragments provide much faster targeting which matches the half-lives of short-lived radionuclides (42, 43). The use of small antibody fragments which specifically bind to the agent causing the infection and which are radiolabeled with short-lived isotopes may be preferred for treatment of acute infections. In different embodiments, the fragment is a F(ab')$_2$ fragment or a Fab' fragment, or a peptide that specifically binds to an agent causing infection.

The dose of the radioisotope can vary depending on the localization of the infection, the severity of infection, the method of administration of radiolabeled antibody (local or systemic) and the decay scheme of the radioisotope. In order to calculate the doses which can significantly decrease or eliminate infection burden without radiotoxicity to vital organs, a diagnostic scan of the patient with the antibody radiolabeled with diagnostic radioisotope or with the low activity therapeutic radioisotope can be performed prior to therapy, as is customary in nuclear medicine. The dosimetry calculations can be performed using the data from the diagnostic scan (57).

Clinical data (34, 51) indicate that fractionated doses of radiolabeled antibodies and peptides are more effective than single doses against tumors and are less radiotoxic to normal organs. Depending on the status of a patient and the effectiveness of the first treatment with RIT, the treatment may consist of one dose or several subsequent fractionated doses.

In one embodiment, the subject is a mouse, and the dose of the radioisotope is between 50-200 µCi. In one embodiment, the subject is a human, and the dose of the radioisotope is between 1-500 mCi.

The concentration of antibody conjugated to the radiolabel which is effective to treat the infection can be less than the concentration of nonconjugated passive antibody which may be used for treatment of the infection.

The subject invention also encompasses treatment of infections caused by other microorganisms. In one example, the infection is a bacterial infection. Examples of bacterial infections include, but are not limited to, infections due to *Bacillus anthracis, Escherichia coli, Mycobacterium tuberculosis, Pneumocystis carinii, Mycobacterium bovis, Bacillus Calmette Guerrin* (BCG) or *Streptococcus pneumoniae*. In a preferred embodiment, the bacterium is *Streptococcus pneumonia* and the antibody is D11. Preferably, the antibody is an IgM antibody. Preferably, the radiation dose that is effective to kill the bacterium is an order of magnitude less than the dose of external gamma radiation that is effective to kill the bacterium. More preferably, the radiation dose that is effective to kill the bacterium is two orders of magnitude less than the dose of external gamma radiation that is effective to kill the bacterium.

In another example, the infection is a viral infection. Examples of viral infections include, but are not limited to, infections due to human immunodeficiency virus (HIV) or a *Variola* virus, which cause smallpox and cowpox. The method of the invention can also be adapted to kill virions or cells that express viral proteins on their surface. Preferably, the radiation dose that is effective to kill the virus is at least two orders of magnitude less than the dose of external gamma radiation that is effective to kill the virus. More preferably, the radiation dose that is effective to kill the virus is at least three orders of magnitude less than the dose of external gamma radiation that is effective to kill the virus.

In a further embodiment, the infection is a parasitic infection. Examples of parasite infections include, but are not limited to, infections due to a *Plasmodium* protozoan which causes malaria, *Trypanosoma brucei* which causes sleeping sickness, *Trypanosoma cruzi* which causes Chagas' disease, and *Toxoplasma gondii* which causes toxoplasmosis. Preferably, the radiation dose that is effective to kill the parasite is an order of magnitude less than the dose of external gamma radiation that is effective to kill the parasite. More preferably, the radiation dose that is effective to kill the parasite is two orders of magnitude less than the dose of external gamma radiation that is effective to kill the parasite.

The invention is also directed to a method of using a radiolabeled antibody to treat an infection in a subject which comprises:

(a) generating a monoclonal antibody against an agent causing the infection;

(b) attaching a radiolabel to the monoclonal antibody; and (c) administering to the subject an amount of the radiolabeled antibody effective to treat the infection, wherein the antibody specifically binds to an agent causing the infection. If an antibody is not available for any particular microorganism or parasite, it can be readily generated without undue experimentation using the standard protocol given below in Experimental Details.

The invention is further directed to a method of using a radiolabeled antibody to treat an infection in a subject which comprises (a) attaching a radiolabel to an antibody that specifically binds to an agent causing the infection; and (b) administering to the subject an amount of the radiolabeled antibody effective to treat the infection.

The invention provides a method of making a composition effective to treat an infection in a subject which comprises admixing a radiolabeled antibody and a carrier, wherein the antibody specifically binds to an agent causing the infection.

The invention provides a composition comprising an amount of a radiolabeled antibody effective to treat an infection in a subject and a carrier, wherein the antibody specifically binds to an agent causing the infection.

As used herein, the term "carrier" encompasses any of the standard pharmaceutical carriers, such as a sterile isotonic saline, phosphate buffered saline solution, water, and emulsions, such as an oil/water or water/oil emulsions.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example I

Susceptibility of Human Pathogens *Cryptococcus neoformans* and *Histoplasma capsulatum* to Gamma Radiation and Radioimmunotherapy with Alpha- and Beta-Emitting Radioisotopes Materials and Methods

*C. neoformans* (CN) and *H. capsulatum* (HC). American Type Culture Collection (ATCC, Manassas, Va.) strains CN 24067 (serotype D, encapsulated), acapsular mutant CAP67 (parent strain B3501) and HC (CIB 1980, a gift from Dr. A. Restrepo, Medellin CN was grown in Sabouraud dextrose broth (Difco Laboratories, Detroit, Mich.) for 24 hrs at 30° C. with constant shaking at 150 rpm. HC was grown in defined media containing 29.4 mM $KH_2PO_4$, 10 mM $MgSO_4\times7H_2O$, 13 mM glycine, 15 mM D-glucose, 3 μM thiamine with shaking at 37° C. Organisms were washed three times with phosphate buffered saline (PBS), pH 7.2 before use.

Antibodies. Monoclonal antibody (mAb) 18B7 ($IgG_1$) binds to CN capsular polysaccharide (11). MAb 9C7 (IgM) binds to a 17 kDa protein antigen on the surface of the HC cell wall (61). MAb MOPC21 (ICN Biomedicals, Aurora, Ohio) was used as an irrelevant isotype-matched control for 18B7 and mAb UNLB (clone 11E10, Southern Biotechnology Associates) for 9C7.

Antibody concentration was determined by absorbance at 280 nm using an extinction coefficient of 1.35 mL/mg×cm. The immunoreactivity of radiolabeled mAb was determined by ELISA as described in (12). Briefly, polystyrene plates were coated with glucuronoxylomannan (GXM) solution (1 μg/mL) and blocked with 1% bovine serum albumin (BSA) in PBS. Radiolabeled mAb was added at a starting concentration of 10 μg/mL and then serially diluted. Bound mAb was detected using alkaline phosphatase conjugated goat anti-mouse $IgG_1$ followed by addition of p-nitrophenyl-phosphate (PNPP) at 1 mg/mL in substrate buffer. Absorbance at 405 nm was measured with a Ceres 900 Hdi reader (Bio-Tek Instruments Inc, Winooski, Vt.).

Radioisotopes and quantification of radioactivity. $^{188}$Re in the form of Na perrhenate ($Na^{188}ReO_4$) was eluted from a $^{188}$W/$^{188}$Re generator (Oak Ridge National Laboratory (ORNL), Oak Ridge, Tenn.). Actinium-225 ($^{225}$Ac) for construction of a $^{225}$Ac/$^{213}$Bi generator was acquired from ORNL. The $^{225}$Ac/$^{213}$Bi generator was constructed using MP-50 cation exchange resin, and $^{213}$Bi was eluted with 0.15 M HI (hydroiodic acid) in the form of $^{213}BiI_5^{2-}$ as described in (15). $Na^{99m}TcO_4$ was purchased from Syncor (Bronx, N.Y.), and $^{111}InCl_3$ was obtained from Iso-Tex Diagnostics, Friendswood, Tex.

The radioactive samples were counted in a dose calibrator if their activity was >5 μCi (185 kBq), and in a gamma counter with or without appropriate dilution if their activity was <5 μCi. A gamma counter (Wallac) with an open window was used to count the $^{188}$Re and $^{213}$Bi samples. Samples containing known activities were counted to obtain experimentally determined conversion factors of 840,000 cpm/μCi (23 cpm/Bq) for $^{188}$Re and 1,500,000 cpm/μCi (41 cpm/Bq) for $^{213}$Bi.

Susceptibility of CN and HC to external gamma radiation. Approximately $10^5$ CN or HC cells were placed in microcentrifuge tubes in 0.5 mL PBS and irradiated at room temperature in a cell irradiator equipped with a $^{137}$Cs source at a dose rate of 30 Gy/min. The cells were exposed to doses of up to 800,000 rad (8000 Gy). To determine if unlabeled antibody might contribute to killing of fungal cells, in several experiments CN or HC cells were irradiated with 0-400,000 rad (4000 Gy) in the presence of 10 μg 18B7 or 9C7 mAb, respectively. The potential protective effect of the polysaccharide capsule surrounding CN cells was investigated by irradiating acapsular CN strain CAP67. Following radiation exposure, $10^3$ cells were removed from each tube, diluted with PBS and plated to determine viability as measured by colony forming units (CFU's). Experiments were performed in duplicate.

Radiolabeling of antibodies with $^{188}$Re and $^{213}$Bi. The widely utilized nuclear medicine practice of "matching pairs" of radiopharmaceuticals calls for the use of diagnostic isotopes (no α- or β-particles emissions, for imaging procedures) with chemistries similar to those of therapeutic isotopes (16). $^{99m}$Tc is "a matching pair" isotope for $^{188}$Re, and $^{111}$In for $^{213}$Bi (16) because of their shared similar chemical properties. Consequently, these isotopes can be used for labeling under identical conditions, and their biodistribution properties are very similar. Hence, the immunoreactivity results obtained with $^{99m}$Tc and $^{111}$In are readily applicable to $^{188}$Re and $^{213}$Bi, respectively.

MAbs were labeled "directly" with $^{188}$Re via reduction of antibody disulfide bonds by incubating the antibody with 75-fold molar excess of dithiothreitol (17) for 40 min at 37° C. followed by centrifugal purification on Centricon-30 or -50 microconcentrators with 0.15 M $NH_4OAc$, pH 6.5. Simultaneously 3-10 mCi (110-370 MBq) $^{188}ReO_4^{31}$ in saline was reduced with $SnCl_2$ by incubation in the presence of Na gluconate, combined with purified reduced antibodies and kept at 37° C. for 60 min. Radioactivity not bound to the antibody was removed by centrifugal purification on Centricon microconcentrators.

For radiolabeling with $^{213}$Bi or $^{111}$In, mAbs were conjugated to bifunctional chelator N-[2-amino-3-(p-isothiocyanatophenyl)propyl]-trans-cyclohexane-1,2-diamine-N, N', N'', N''', N''''-pentaacetic acid (CHXA'') as in (13, 15, 16), with the average number of chelates per antibody ranging from 0.7 to 3.0 as determined by the Yttrium-Arsenazo III spectrophotometric method (14). CHXA''-conjugated mAb's were radiolabeled with $^{213}$Bi by incubating them for 5 min with $^{213}BiI_5^{2-}$ at room temperature. If required, the radiolabeled antibodies were purified by size exclusion HPLC (TSK-Gel® G3000SW, TosoHaas, Japan).

In vitro radioimmunotherapy of CN and HC with radiolabeled antibodies. $^{188}$Re- or $^{213}$Bi-radiolabeled mAbs 18B7 and 9C7 were used to determine the susceptibility of CN and HC to RIT, respectively, in vitro. MAbs MOPC21 and UNLB were radiolabeled in the same manner and served as isotype matching controls for 18B7 and 9C7, respectively. The cells were incubated at 37° C. for 30 minutes in PBS containing 10 μg $^{188}$Re-mAb (0-32 μCi (1.2 MBq)) or $^{213}$Bi-mAb (0-3.2 μCi (0.12 MBq)) to allow time for the radiolabeled antibodies to bind to the cell surfaces. For control, CN or HC cells were incubated with 10 μg pre-reduced or CHXA''-conjugated unlabeled mAbs. To measure the kinetics of antibody binding to the cells, aliquots of cell suspension were removed at 0, 10, 20 and 30 min, centrifuged to separate the cell pellet from the supernatant, and the cell pellet was counted in a gamma counter. After 30 min incubation with the antibodies, the cells were washed free of extracellular activity and maintained in suspension on a rocker at 4° C. in PBS for a period of either 1 or 48 h for $^{213}$Bi-mAbs or $^{188}$Re-mAbs, respectively. The cells were not dividing during the incubation and maintenance periods because they were maintained in PBS, which lacks nutrients. To ascertain that the radioactivity remained bound to the cells at the end of the 1 or 48 h incubation period, aliquots of cell suspension were removed, counted in gamma counter, followed by centrifugation to separate the cell pellet from the supernatant, washing with PBS and counting of the cell pellet in a gamma counter. At the end of incubation $10^3$ cells were plated for CFU's and the colonies counted after 48 h at room temperature.

Cellular dosimetry. Following the general formalism for cellular dosimetry given by Equation 7 in (62), the mean absorbed dose to the cell from cellular radioactivity is given by $$D_c = \tilde{A} \sum_j b_j S_j(C \leftarrow CS),$$ (Equation 1.1)

where $\tilde{A}$ is the cellular cumulated activity, $b_j$ is the branching ratio of the $j^{th}$ radionuclide in the decay series, and $S_j(C \leftarrow CS)$ is the cellular S value (absorbed dose to the cell per unit cumulated activity) for the $j^{th}$ radionuclide localized on the cell surface (CS) of the cell (C). The cumulated activity $\tilde{A}$ can be written as $$\tilde{A} = \tilde{A}_I + \tilde{A}_M + \tilde{A}_{CF}$$ (Equation 1.2), where $\tilde{A}_I$, $\tilde{A}_M$, and $\tilde{A}_{CF}$ are the cellular cumulated activities during the periods of incubation for cellular uptake of radioactivity, maintenance at 4° C., and colony formation, respectively.

Flow cytometry. Flow cytometry can be used to identify cells undergoing apoptosis. Following gamma irradiation or RIT, the cells were permeabilized and fixed with 70% ethanol, cellular RNA was destroyed by treatment with RNase A at 50° C. for 1 h, the DNA was stained with propidium iodide at pH 7, and the fluorescence per cell was measured in a flow cytometer (63).

Serum stability of radiolabeled 18B7. $^{99m}$Tc-18B7, $^{188}$Re-18B7 and $^{111}$In—CHXA"-18B7 were incubated in human serum for 24 hours. At different times aliquots were analyzed on size exclusion HPLC column eluted with PBS, pH 7.2 at 1 mL/min. Proteins were monitored at 280 nm; 1 mL fractions were collected and counted in a Capintec dose calibrator (E. R. Squibb and Sons, Inc., Princeton, N.J.).

Biodistribution of $^{99m}$Tc-18B7 in CN-infected BALB/c mice. Six to eight-week old female BALB/c mice were infected intratracheally as described (18). The intratracheal model was used in the biodistribution study because it allows one to induce an infection that is initially localized to one organ, which facilitates the imaging of the infectious process if the antibody localizes to that site. An IV infection is not ideal for biodistribution studies because all organs are affected, so antibody localization would be extremely difficult to demonstrate with the techniques used. BALB/c mice are more resistant than A/JCr mice to C. neoformans infection and their use in the pulmonary model has the advantage that dissemination does not occur early, with the localized infection facilitating imaging studies.

Mice were anesthetized with a mixture of 125 mg/kg ketamine and 10 mg/kg xylazine and inoculated with $10^6$ CN cells into the trachea following exposure via a midline neck incision using a 26-gauge needle attached to a tuberculin syringe. On the 5$^{th}$ day after infection, 3 mice were pretreated with 1.0 mg 18B7 to bind the excess of capsular polysaccharide (CPS) in circulation. 1.5 hours later, 3 infected and 3 infected/pretreated mice were injected IV with 0.125 mCi (0.05 mg) of $^{99m}$Tc-18B7. A group of 3 healthy mice was injected with the same amount of radiolabeled conjugate and served as a control. At 24 hours animals were sacrificed, their major organs removed, weighed and counted in a gamma-counter (Wallace, Finland).

Treatment of A/JCr mice infected with CN with radiolabeled mAbs. Nine groups of 10 A/JCr female mice (National Cancer Institute, Frederick, Md.) were infected IV with $10^5$ CN cells (79). The IV infection model results in rapid death and is the standard model used for antifungal susceptibility testing. The intratracheal infection model was not used for the therapeutic studies because it results in a chronic infection that can be very prolonged, such that mice infected intratracheally can live up to 1 year (18). 24 hours after infection groups #1, 2 and 3 received IP injections of 50, 100 and 200 μCi $^{213}$Bi—CHXA"-18B7, respectively; group #4- 100 μCi $^{213}$Bi—CHXA"-MOPC21; groups #5, 6 and 7-50, 100 and 200 μCi $^{188}$Re-18B7, respectively; group #8-100 μCi $^{188}$Re-MOPC21. The amount of antibody per injection was 30-50 μg, the injection volume was 0.1-0.25 mL PBS. Group #9 received 0.1 mL PBS and group #10 received 50 μg "cold" 18B7 in 0.1 mL PBS. The animals were observed for their vital signs daily and survival was recorded every 24 hours for 75 days.

Determination of organ CFUs. A group of 15 A/JCr female mice were infected IV with $10^5$ CN cells. At 24 hours after infection the mice were separated in groups of three and groups #1, 2 and 3 received IP injections of 50, 100 and 200 μCi $^{188}$Re-18B7, respectively. The amount of antibody per injection was 30-50 μg, injection volume—0.1-0.25 mL PBS. Group #4 received 50 μg "cold" 18B7 in 0.1 mL PBS and control group #5 was left untreated. 48 hours after treatment the animals were sacrificed, their lungs and brains removed, blotted to remove excess blood, counted in a gamma counter, weighed, homogenized in 2 mL PBS, and dilutions of the homogenate plated to determine CFUs.

Statistics. The Wilcoxon Rank Sum test was used to compare organs uptake in biodistribution studies. Student's t test for unpaired data was employed to analyze differences in the number of CFUs between differently treated groups during in vitro therapy studies. The log-rank test was utilized to assess the course of animal survival. Differences were considered statistically significant when P values were<0.05.

Results

Radiolabeling of 18B7 mAb. Various techniques were evaluated for attaching $^{188}$Re and $^{213}$Bi to 18B7 mAb. In some preliminary experiments 99m-Technetium ($^{99m}$Tc) and 111-Indium ($^{111}$In) were used as substitutes for $^{188}$Re and $^{213}$Bi, respectively, because of their quite similar chemical properties and availability. Direct labeling of 18B7 mAb with $^{99m}$Tc and $^{188}$Re through generation of thiol groups resulted in 90±5% and 87±4% yields for $^{99m}$Tc and $^{188}$Re, respectively. Radiolabeling yields for CHXA"-18B7 with $^{111}$In and $^{213}$Bi were 90±4%. Subsequent purification on Centricon-30 microconcentrators or by size exclusion HPLC gave products with radiochemical purity of 97±1%.

Figure 1B:
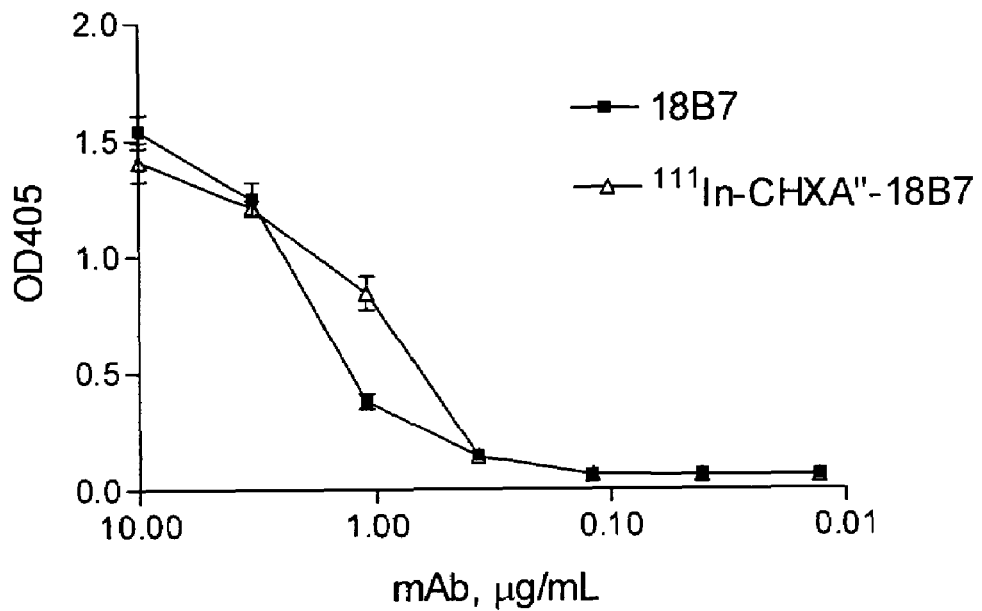

Immunoreactivity of radiolabeled 18B7 mAb. The mAb 18B7 binds to the CN GXM (12), which is the major capsular polysaccharide. This mAb proved to be a robust molecule that could be labeled with a variety of radioisotopes without a loss of immunoreactivity via either direct labeling or using a bifunctional chelating agent. The results of immunoreactivity measurements of radiolabeled 18B7 are shown in FIGS. 1A-1B. Direct labeling had little or no effect on the immunoreactivity of 18B7 mAb, since >90% of radiolabeled 18B7 bound to GXM antigen. For CHXA"-18B7 conjugates, the 1.5 ligand to mAb molar ratio in the conjugation reaction resulted in 0.7-0.9 ligand per mAb molecule, which preserved its immunoreactivity. These results show the feasibility of chemically modifying mAb 18B7 while retaining its ability to bind to CN.

Serum stability of radiolabeled 18B7. 99mTc-18B7, 188Re-18B7 and 111In—CHXA"-18B7 conjugates were analyzed by size exclusion HPLC after incubation in human serum at 37° C. for 24 hours. Size exclusion HPLC revealed that little radioactivity was lost from the 99mTc-18B7 and 188Re-18B7 in the form of small molecular size radioactive species. 111In—CHXA"-18B7 did not release any radioactivity during 24 hours incubation in human serum. These data demonstrated that the radiolabeled mAb 18B7 is stable in serum.

Figure 2A:
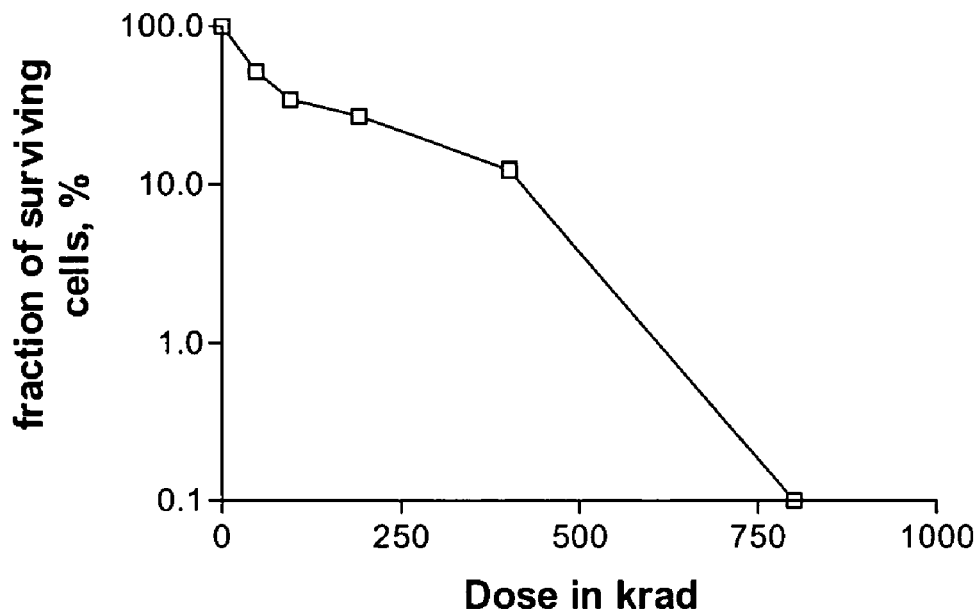
FIGS. 2A-2B. Resistance of fungi (*Cryptococcus neoformans* and *Histoplasma Capsulatum*) to external gamma radiation. Fraction of surviving cells shown as a function of radiation dose ($^{137}$Cs source, 3,000 rad/min, 30 Gy/min). A) *Cryptococcus neoformans* (CN); B) *Histoplasma capsulatum* (HC).
Figure 2B:
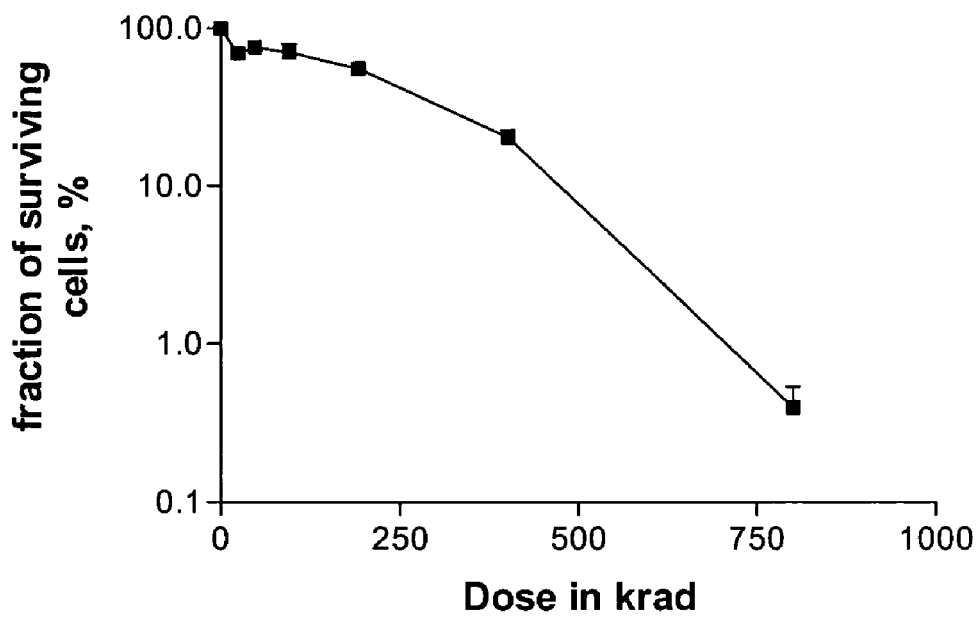

Resistance of CN and HC to external gamma radiation. Both CN and HC were very resistant to the effects of gamma radiation (80), with 10% of the cells surviving at the doses of ~400 krad (4000 Gy), and less than 1% surviving a dose of ~800 krad (8000 Gy) (FIGS. 2A-2B).

Figure 3:
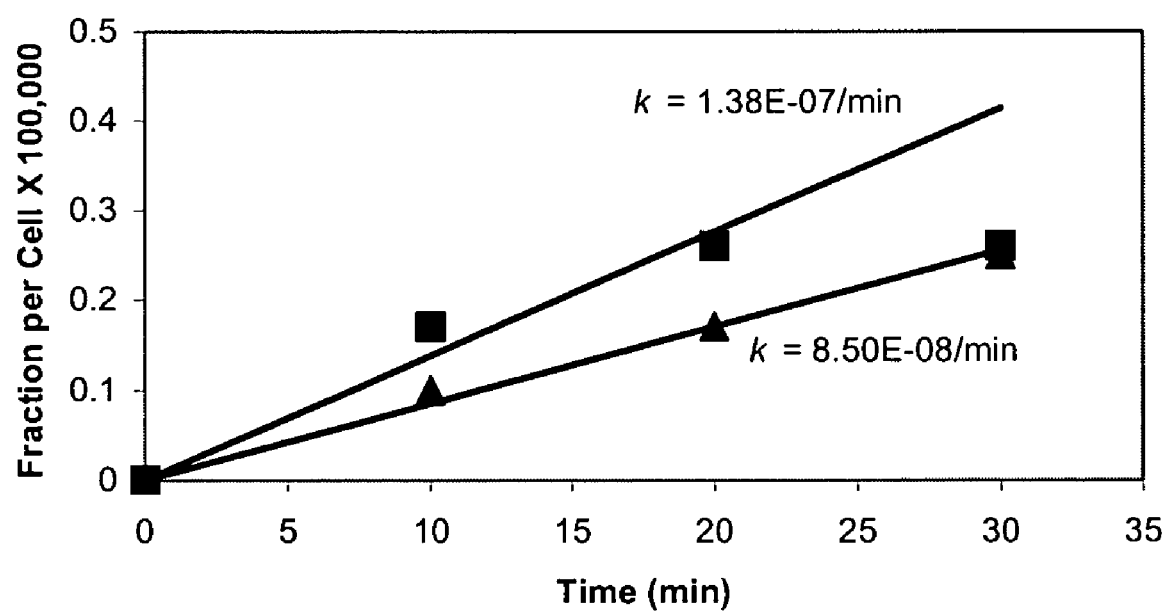
FIG. 3. Kinetics of binding of $^{188}$Re-18B7 mAb (▲) and $^{188}$Re-9C7 mAb (■) to the cell surfaces of CN and HC, respectively. The $^{188}$Re-18B7 mAb data are fitted to a linear function with a resulting slope of k=8.50E-08 min$^{-1}$. The $^{188}$Re-9C7 data up to a time of 20 minutes are similarly fitted with a resulting slope of k=1.38E-07 min$^{-1}$. MAb 18B7 has IgG1 isotype, and 9C7 has IgM isotype.

Kinetics of radiolabeled antibodies binding to CN and HC cells. During the incubation period, the cellular uptake of radioactivity was linear in time up to 30 min for CN cells (FIG. 3). Some saturation in the cellular uptake was observed in the case of HC (FIG. 3). Least squares fits of these data are provided in the caption for FIG. 3. There was no measurable detachment of radiolabeled antibodies from the surface of the cells after incubation in PBS for either 1 or 48 h.

Cellular dosimetry. Cumulated Activity during Incubation Period (Cellular Uptake at 37° C.). According to Makrigiorgos et al. (64), when the cellular uptake is linear in time and there is no biological elimination of the radioactivity, the cellular radioactivity at time t of the incubation period is given by $$A_I(t) = kA_o t e^{-\lambda t} \quad \text{(Equation 1.3)}$$

where k is a constant of proportionality determined experimentally, $A_o$ is the initial activity added to the tube containing the cells, and $\lambda$ is the physical decay constant for the radionuclide ($\lambda = 0.693/T_p$, where $T_p$ is the physical half-life). Makrigiorgos et al. (64) have also shown that the cumulated activity at time $t=t_I$ is given by $$\tilde{A}_I(t = t_I) = \frac{k}{\lambda^2} A_o \{1 - (1 + \lambda t_I) e^{-\lambda t_I}\}. \quad \text{(Equation 1.4)}$$

Cumulated Activity during Maintenance Period (4° C.). The activity present in the cell at the beginning of the maintenance period is given by $$A_M(t_I) = kA_o t_I e^{-\lambda t_I} \quad \text{(Equation 1.5)}$$

Assuming no biological elimination of the radioactivity from the cells, the cellular activity as a function of time t during the maintenance period is then $$A_M(t) = kA_o t_I e^{-\lambda t_I} e^{-\lambda t} \quad \text{(Equation 1.6)}$$

The cumulated activity during the maintenance period $t_M$ is then given by $$\tilde{A}_M(t = t_M) = \quad \text{(Equation 1.7)}$$

$$kA_o t_I e^{-\lambda t_I} \int_o^{t_M} e^{-\lambda t} dt = \frac{k}{\lambda} A_o t_I e^{-\lambda t_I} (1 - e^{-\lambda t_M}).$$

Cumulated Activity during Colony Forming Period (Room temperature). Finally, assuming that the activity is eliminated from the cells by both biological processes of an exponential nature and physical decay, the activity present in the cell at time t during the colony forming period is given by $$A_{CF}(t) = kA_o t_I e^{-\lambda t_I} e^{-\lambda t_M} e^{-\lambda_e t} \quad \text{(Equation 1.8)}$$

The quantity $\lambda_e$ is the effective decay constant where $\lambda_e = \lambda + \lambda_b$, and $\lambda_b$ is the biological disappearance constant (65). The cumulated activity during the colony forming period $t_{CF}$ is therefore given by $$\tilde{A}_{CF}(t = t_{CF}) = kA_o t_I e^{-\lambda t_I} e^{-\lambda t_M} \int_o^{t_{CF}} e^{-\lambda_e t} dt = \quad \text{(Equation 1.9)}$$

$$\frac{k}{\lambda_e} A_o t_I e^{-\lambda t_I} e^{-\lambda t_M} (1 - e^{-\lambda_e t_{CF}}).$$

Figure 4:
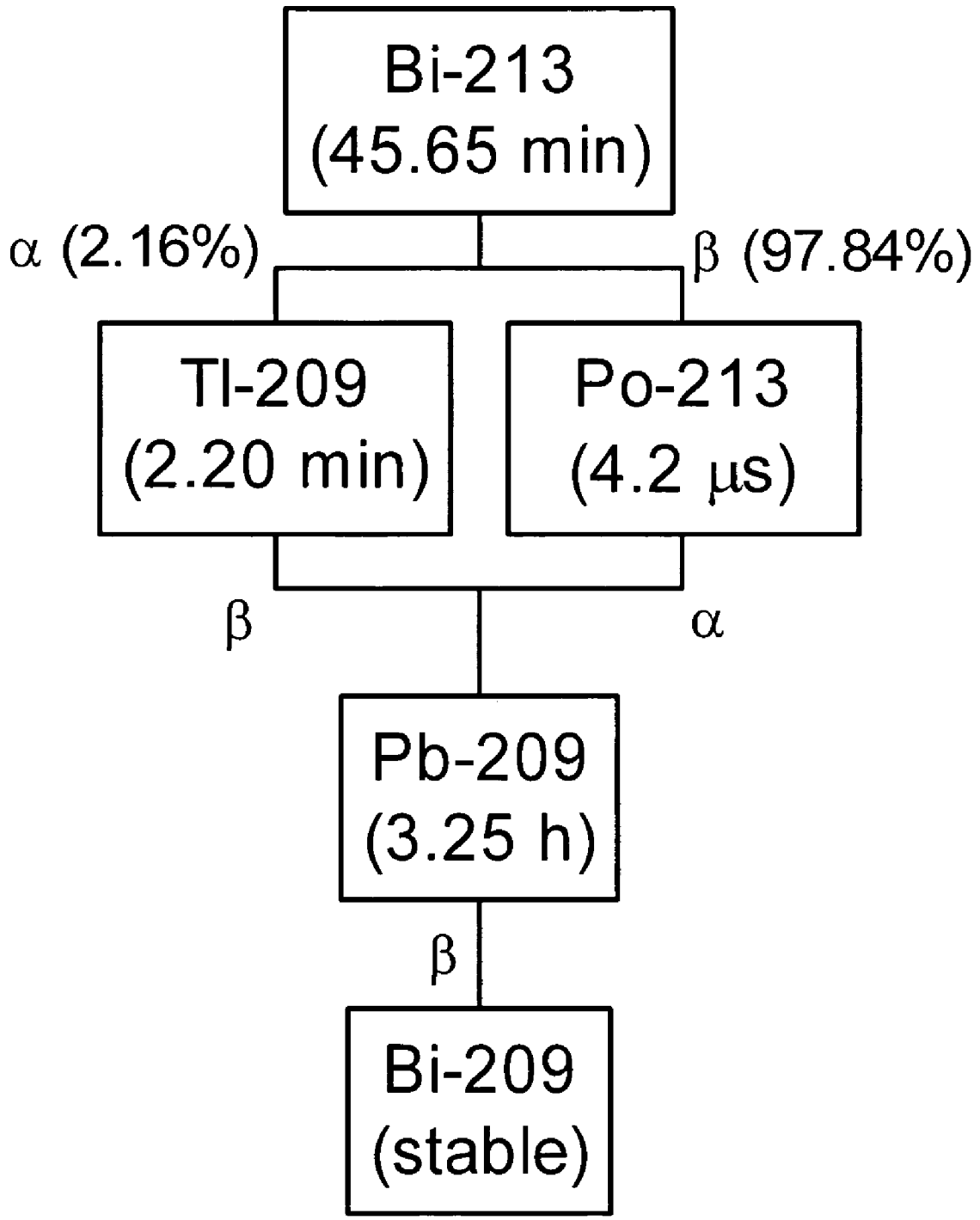
FIG. 4. Decay series of $^{213}$Bi. Physical half-lives and branching ratios are taken from (62).

Cellular S Values and Physical Decay Constants. The cellular S values are obtained from the tabulations in the Society of Nuclear Medicine's Cellular S Values monograph (62). Since the antibodies remain on the cell surfaces, only $S(C \leftarrow CS)$ is required. The radii of the CN and HC cells are approximately 10 μm and 5 μm, respectively. The corresponding S values for $^{188}$Re are $6.82 \times 10^{-5}$ and $3.34 \times 10^{-4}$ Gy Bq$^{-1}$s$^{-1}$ for CN and HC, respectively. As expected, the cellular S values are quite sensitive to cell size. Deciding which S values are required for $^{213}$Bi dosimetry is more complex due to its decay to various daughter radionuclides (FIG. 4). The violence of the $^{213}$Bi alpha decay can be assumed to disrupt the radionuclide-antibody bond with consequent departure of the daughter $^{209}$Tl from the cell surface before it has a chance to decay. The same is assumed for $^{209}$Pb, the daughter of $^{213}$Po. Therefore, only S values for $^{213}$Bi and $^{213}$Po are required. For $^{213}$Bi localized on the surface of cells having radii of 10 μm and 5 μm, $S(C \leftarrow CS)$ is $4.14 \times 10^{-4}$ and $1.64 \times 10^{-3}$ Gy Bq$^{-1}$s$^{-1}$, respectively. No S values are tabulated in (62) for $^{213}$Po which emits an 8.375 MeV alpha particle. Interpolation of the cellular S values for alpha particles given in Appendix III of Cellular S Values (62) gives $S(C \leftarrow CS) = 1.21 \times 10^{-2}$ and $4.74 \times 10^{-2}$ Gy Bq$^{-1}$s$^{-1}$ for $^{213}$Po on the surface of cells with radii of 10 and 5 μm, respectively. The physical decay constants for a radionuclide is given by $\lambda = 0.693/T_p$, where $T_p$ is the physical half-life. Therefore, $\lambda(^{188}\text{Re}) = 6.80 \times 10^{-4}$ min$^{-1}$ and $\lambda(^{213}\text{Bi}) = 1.52 \times 10^{-2}$ min$^{-1}$.

*Cryptococcus neoformans*, $^{188}$Re-18B7 mAb. The incubation period $t_I = 30$ min, maintenance period $t_M = 48$ h = 2880 min, and $t_{CF} = 2880$ min. There is no cell division during $t_I$ or $t_M$ so no biological elimination occurs during these periods. Thus, substituting $k = 8.5 \times 10^{-8}$ min$^{-1}$ and the various parameters into Equations 1.4 and 1.7 gives $\tilde{A}_I = 0.00226 A_o$ s and $\tilde{A}_M = 0.189 A_o$ s. The CN cells form colonies through a budding process. Due to the nature of this budding process, it is expected that a negligible amount of radioactivity is passed from the parent cell to the daughter cells (66). Thus, it is assumed that all radioactivity remains with the parent. Substituting the various parameters into Equation 1.9 gives $\tilde{A}_{CF} = 0.0267 A_o$ s. Finally, as per Equation 1.2, the sum is $\tilde{A} = \tilde{A}_I + \tilde{A}_M + \tilde{A}_{CF} = 0.218 A_o$ s. The absorbed dose is given by Equation 1.1 where $D_C = \tilde{A} S(C \leftarrow CS) = 0.218 A_o$ s ($6.82 \times 10^{-05}$ Gy/Bq s) = $0.0149 A_o$ Gy, where $A_o$ is the kBq added to the tube of cells.

*Cryptococcus neoformans*, $^{213}$Bi-18B7 mAb. Substituting $k = 8.5 \times 10^{-8}$ min$^{-1}$, $\lambda(^{213}\text{Bi}) = 1.52 \times 10^{-2}$ min$^{-1}$, $t_I = 30$ min, $t_M = 60$ min, and $t_{CF} = 2880$ min into Equations 1.4 and 1.7 gives $\tilde{A}_I = 0.00170 A_o$ s, $\tilde{A}_M = 0.00382 A_o$ s, and $\tilde{A}_{CF} = 0.00256 A_o$ s. The total cumulated activity $\tilde{A} = 0.00808 A_o$ s. Assuming that only the $^{213}$Bi and $^{213}$Po decays deposit energy in the cell and that $^{213}$Po is in equilibrium with $^{213}$Bi, Equation 1.1 gives $D_C = \tilde{A}(S(^{213}\text{Bi}, C \leftarrow CS) + 0.9784 \, S(^{213}\text{Po}, C \leftarrow CS))$. Substitution of the S values gives $D_C = 0.0990$ Gy per kBq of $^{213}$Bi added to the tube.

*Histoplasma capsulatum*, $^{188}$Re-9C7 mAb. The uptake of this mAb is reasonably linear up to 20 min, therefore the dosimetry can be simplified by taking $t_I = 20$ min. The remaining 10 min of this period can then be added to the maintenance period so that $t_M = 2890$ min. Finally, as before, $t_{CF} = 2880$ min.

There is no biological elimination during $t_I$ or $t_M$ so only physical decay occurs during these periods. Substituting $k=1.38\times10^{-7}$ min$^{-1}$ (FIG. 3) and the various parameters into Equations 1.4 and 1.7 gives $\tilde{A}_I=0.00164\,A_o$ s and $\tilde{A}_M=0.207\,A_o$ s. During cell division, which takes about 2 h, the membrane is shared between parent and daughter HC cells. Therefore, it is assumed that the bound radioactivity is divided between the two cells. Consequently, the effective half time of the radioactivity in the cell during the colony forming period is $\lambda_e=\lambda+\lambda_b=6.8\times10-4$ min$^{-1}+0.693/120$ min$^{-1}=0.00646$ min$^{-1}$. Substituting the various parameters into Equation 1.9 gives $\tilde{A}_{CF}=1.77\times10^{-4}\,A_o$ s. Finally, as per Equation 1.2, the sum is $\tilde{A}=\tilde{A}_I+\tilde{A}_M+\tilde{A}_{CF}=0.209\,A_o$ s. The absorbed dose is given by Eq. 1.1 where $D_C=\tilde{A}\,S(C\leftarrow CS)=0.209\,A_o$ s (3.34× $10^{-4}$ Gy/Bq s)=0.0698 $A_o$ Gy where $A_o$ is the kBq added to the tube of cells.

Figure 5A:
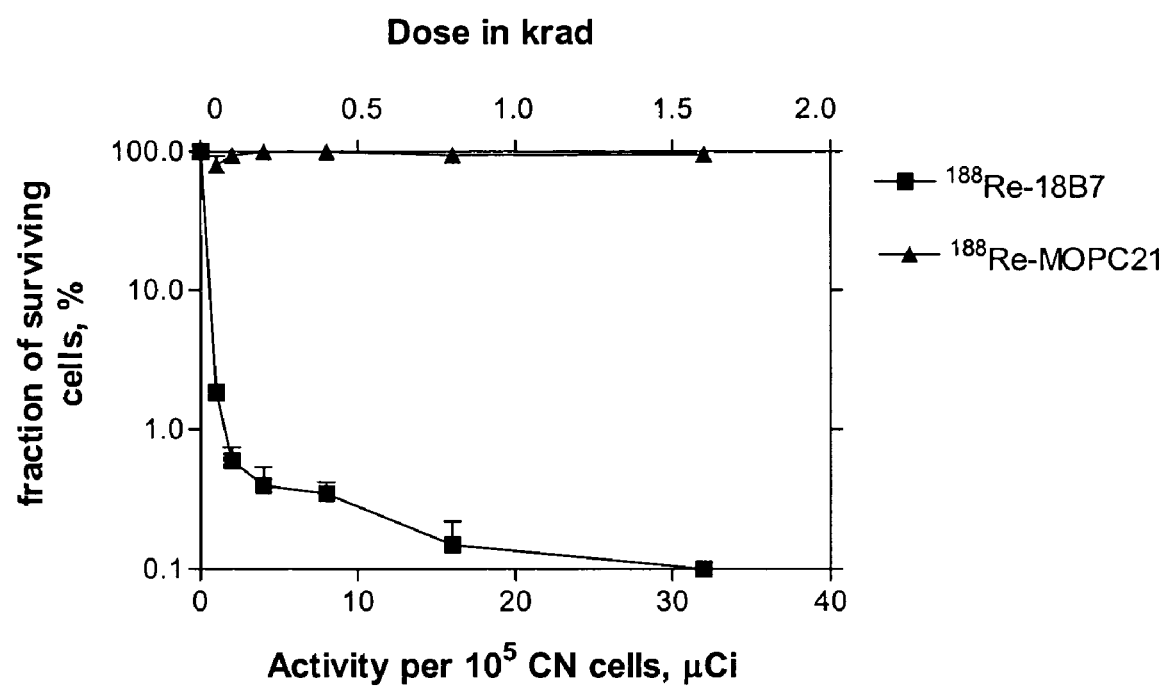
FIGS. 5A-5C. Cell survival of fungi following in vitro radioimmunotherapy. A) CN with $^{188}$Re-18B7 mAb; B) CN with $^{213}$Bi-18B7 mAb; C) HC with $^{188}$Re-9C7 mAb.
Figure 5B:
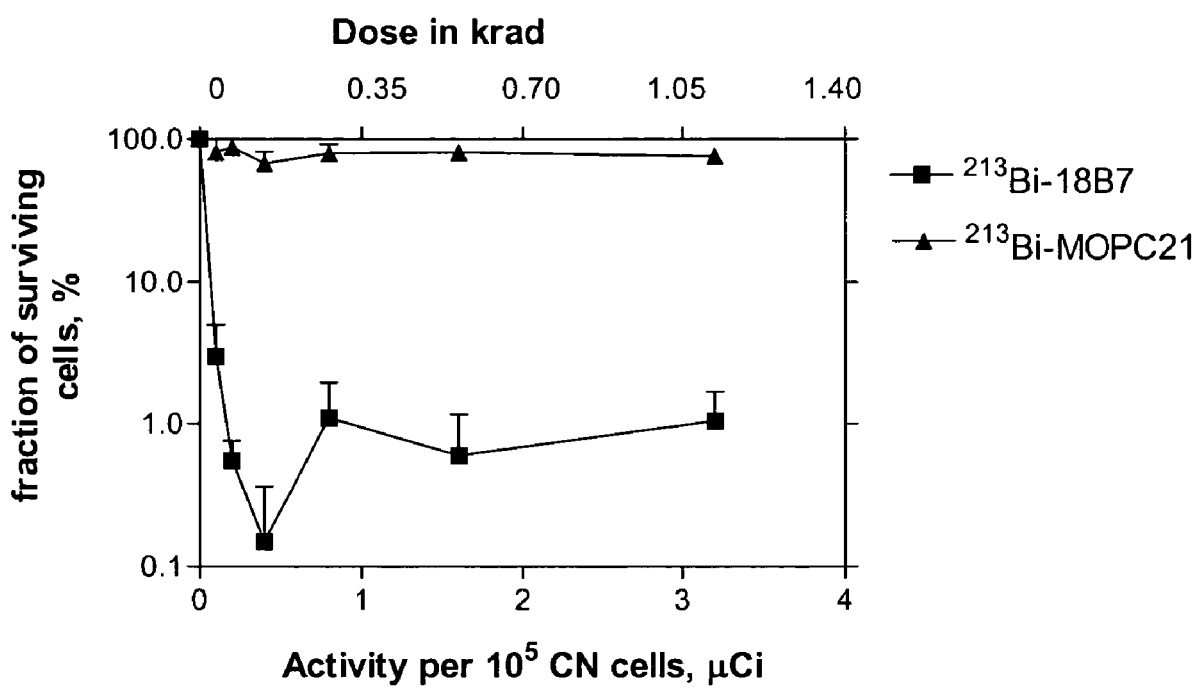

Susceptibility of CN and HC to RIT with $^{188}$Re- and $^{213}$Bi-radiolabeled antibodies in vitro. The RIT of CN cells was performed with both $^{188}$Re- and $^{213}$Bi-radiolabeled antibodies. The RIT of HC was carried out only with $^{188}$Re-labeled antibodies as 9C7 mAb proved to be not amenable to conjugation with CHXA" for further radiolabeling with $^{213}$Bi. The dependence of the RIT-treated CN and HC cell survival upon radioactivity added to the cells and the cellular absorbed dose delivered by radiolabeled antibodies is presented in FIGS. 5A-5C. Control experiments demonstrated that unlabeled mAb's in either pre-reduced form or conjugated with CHXA" did not cause death of fungal cells. Interestingly, in the case of CN the doses of ~0.2 and 0.100 krad (2 and 1 Gy) for $^{188}$Re-18B7 and $^{213}$Bi-18B7, respectively, eradicated more than 99% of CN cells (FIGS. 5A, 5B). In contrast, radiolabeled control antibody MOPC21 with the same specific activity produced only minimal killing within the investigated range of doses (P<0.001). The killing that accompanies incubation of the irrelevant mAb with CN presumably reflects fungal damage from the radioactivity homogeneously distributed in the well. The significantly higher killing associated with the specific antibody almost certainly reflects higher radiation exposure for CN as a consequence of antibody binding to the CN capsule.

The in vitro therapy experiments clearly demonstrated the utility of RIT. One should also bear in mind that during in vitro therapy experiments a very high percentage of β-radiation emitted by $^{188}$Re is deposited outside of the cell, since $^{188}$Re β-particles have a range in tissue of ~5 mm and the radius of the CN capsule is only 20±6 μm (19). In vivo, on the contrary, as the density of the microorganisms in infectious foci increases, the absorbed dose from $^{188}$Re will increase exponentially. Also, even if a particular cell has not been targeted with a radiolabeled antibody molecule, it may be killed by radiation from a distant cell by the so-called "cross-fire" effect. Nevertheless, even under suboptimal in vitro conditions the antibody-specific effective treatment of CN cells in suspension with $^{188}$Re-18B7 was observed.

As the relative biological effectiveness (RBE) of α-particles is several times higher than that of β's (1), 10 times lower radioactivity concentration in the treatment of CN with $^{213}$Bi-labeled antibodies was used in comparison to treatment with $^{188}$Re. Minimal inhibitory concentration (MIC) for $^{213}$Bi—CHXA"-MOPC21 was determined to be 0.4 μci/1.5 μg 18B7 mAb. The fungicidal activity of the irrelevant mAb $^{213}$Bi—CHXA"-MOPC21 was negligible (P=0.0006) at the activity concentrations studied. This result attests to a very high killing efficiency of $^{213}$Bi towards CN, as high linear energy transfer (LET) of α-particles makes it possible to kill a cell with 1-2 hits (several hundred hits per cell are needed when β-emitting radionuclides are used).

There was no statistically significant difference between CFU numbers at 0.5 μCi and at higher activities (P>0.05), as a consequence of very low numbers of colonies in the treated samples due to massive killing of yeast cells.

Flow cytometry. The results of flow cytometry analysis of apoptosis in non-irradiated, irradiated with gamma rays and treated with RIT are presented in Table 1 for both CN and HC cells. Exposure of fungal cells to 400 krad (4000 Gy) of gamma radiation caused apoptosis in a significant percentage of CN and HC cells. Strikingly, RIT of CN with $^{213}$Bi-18B7 caused 80-90% of the cells to die through apoptotic pathway which is consistent with the very low survival rate of $^{213}$Bi-18B7-treated cells at the highest dose of 1.17 krad (11.7 Gy) (FIG. 5B).

Biodistribution of $^{99m}$Tc-18B7 mAb in CN-infected BALB/c mice. Table 2 summarizes the biodistribution results in intratracheally-infected and control mice at 24 hour following injection of labeled antibody. The uptake of $^{99m}$Tc-18B7 in the blood, liver, kidney and spleen in infected mice was higher than in infected mice pretreated with 1 mg unlabeled mAb 18B7 or in the control animals (P<0.05). This may be due to the longer circulation of radiolabeled antibody-antigen complex in the blood relative to antibody alone. The uptake in the lungs and the spleens of infected animals was 2 times higher than observed in control mice or in infected/pretreated mice (P<0.05). Interestingly, there were no significant differences in the lungs and spleen uptakes of mice pretreated with unlabeled mAb 18B7 and controls (P=0.8). These results can be attributed to epitope blocking in the target site by unlabeled antibody. No significant release of $^{99m}$Tc radiolabel occurred as indicated by the low uptake in the stomach. By 24 hour post-injection~10% ID/g was delivered to the lungs infected with CN, a dose that should be sufficient to deliver fungicidal levels of therapeutic radioisotopes to the infectious foci. The relatively high lung uptake (4-5%) of radiolabeled 18B7 in the pre-treated and control animals may be due to uptake by pulmonary cells, including macrophages.

Treatment with radiolabeled mAbs of A/JCr mice lethally infected with CN. The efficacy of RIT against CN infection was tested in A/JCr mice. This mouse strain was selected because it is very susceptible to CN infections, presumably because of partial complement deficiency (21). Mice with partial complement deficiency succumb rapidly with disseminated infection when infected IV (22).

Figure 6A:
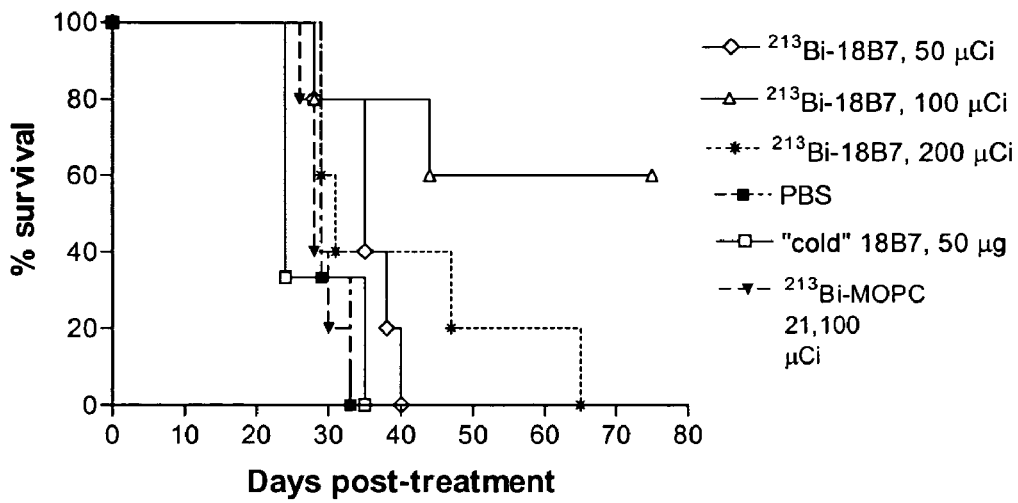
FIGS. 6A-6B. Kaplan-Meier survival curves for A/JCr mice infected IV with $10^5$ *C. neoformans* cells 24 hours prior to treatment with: A) 50-200 µCi $^{213}$Bi-labeled mAb's, and B) 50-200 µCi $^{188}$Re-labeled mAbs. Animals injected with PBS (phosphate buffered saline) or 50 µg "cold" 18B7 served as controls. Survival studies were performed twice.
Figure 6B:
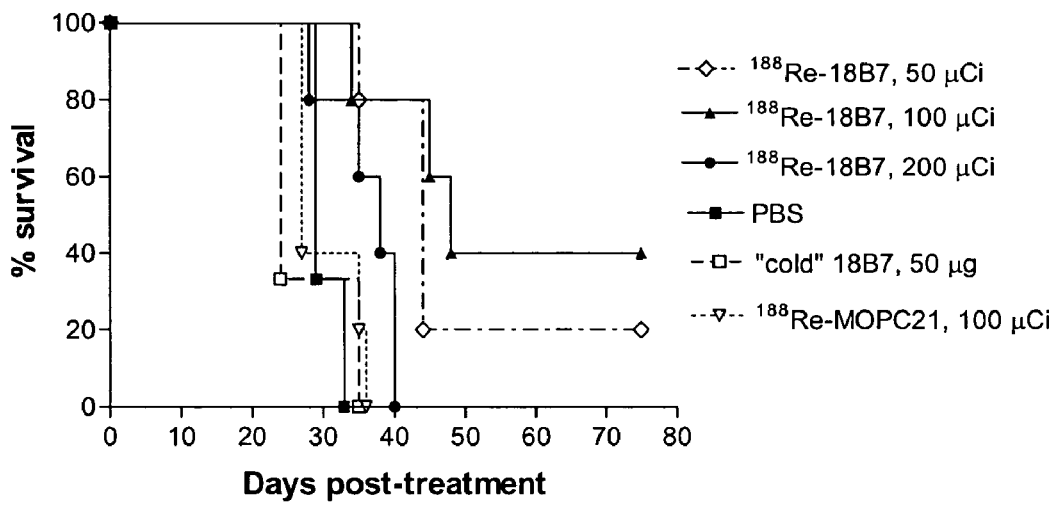

No prolongation in survival was observed in animals treated with unlabeled mAb 18B7 (FIGS. 6A-6B and Table 3) relative to mice given no antibody treatment (PBS) group (P>0.05). There are two explanations for the lack of efficacy of "cold" antibody. First, only a very small amount (30-50 μg) was given. The IV infection model is rapidly lethal and administration of "cold" antibody is therapeutic only if given shortly after infection and in large amounts (e.g. 1 mg) (22). Second, the efficacy of "cold" antibody drops dramatically when given after infection in this model, a finding that is commonly observed when therapeutic antibodies are tested in animal models of infection (23). For example, even large amounts of "cold" antibody were ineffective in prolonging survival of IV infected mice when given after infection (22).

Similarly, the $^{213}$Bi-or $^{188}$Re-labeled IgG$_1$ MOPC21 used as an irrelevant control did not prolong survival relative to untreated mice. A labeled irrelevant mAb was used to control for the possibility that Fc receptor binding by the radiolabeled IgG to phagocytes at the site of infection might result in non-specific killing. On the other hand, animals treated with radiolabeled CN-specific mAb 18B7 lived significantly longer, on average, than mice given irrelevant labeled IgG1 or PBS. Remarkably, on day 75 post-therapy 60% of mice in $^{213}$Bi group were alive after treatment with 100 μCi $^{213}$Bi—CHXA"18B7 (P<0.05). In the $^{188}$Re group 40% and 20% of animals were alive after treatment with 100 (P<0.005) and 50 μCi (P<0.05) $^{188}$Re-18B7, respectively.

To evaluate the "therapeutic window" of RIT for CN infection in A/JCr mice, antibody amounts were administered corresponding to a range of activities—from 50 to 200 μCi per animal, which represents a 4-fold (or 300%) increase in dose. In contrast to treatment with antibiotics, increasing the RIT dose by several-fold will often not improve the survival of the host, but on the contrary, will result in death due to radiation injury. Hence, in experimental RIT maximum tolerated activity (MTA) is usually defined as the highest possible activity under the respective conditions that does not result in any animal deaths, with the next higher dose level resulting in a least 10% of the animals dying from radiation injury (24). The large therapeutic window for RIT of murine infection is evident from the fact that the MTAs for cancer therapy are usually determined by increasing the activities administered in 15-20% increments (25) whereas a 4-fold difference in dosing was evaluated in the subject study.

Survival of A/JCr mice was also dose dependent for $^{213}$Bi and $^{188}$Re radioisotopes: while 50 μCi $^{213}$Bi—CHXA"-18B7 failed to produce any therapeutic effect, both 100 and 200 μCi dosed prolonged animal survival. Interestingly, the 200 μCi $^{213}$Bi—CHXA"-18B7 dose was less efficient, probably, due to approaching the MTA for this particular combination of antibody and radioisotope. In the $^{188}$Re group, administration of 50 μCi $^{188}$Re-18B7 resulted in some prolongation of survival, 100 μCi caused significant prolongation, and 200 μCi dose was, apparently, too toxic with all animals dying by day 40.

The RIT protocol used in these experiments is theoretically capable of delivering a radioactive atom to every CN cell in this animal model. At the time interval of 24 hours after IV infection with $10^5$ CN cells there is a maximum of $4 \times 10^8$ CN yeast cells in the host, assuming a 2 hour doubling time with no cell killing by host defenses. Doses of 50, 100 and 200 μCi $^{213}$Bi—CHXA"-18B7 contain $7.5 \times 10^9$, $1.5 \times 10^{10}$, and $3 \times 10^{10}$ $^{213}$Bi atoms, respectively; 50, 100 and 200 μCi $^{188}$Re-18B7–$1.61 \times 10^{11}$, $3.2 \times 10^{11}$, and $6.4 \times 10^{11}$ $^{188}$Re atoms, respectively.

Treatment with radiolabeled antibodies reduced organ CN burden. Table 4 shows CN CFUs in the lungs and the brains of A/JCr mice infected IV with $10^5$ CN organisms and treated with $^{188}$Re-18B7 mAb 24 hours after infection. Mice infected with CN and given RIT had significantly reduced fungal burden in lungs and brains. The counting of the brains and lungs in a gamma counter showed that radioactivity delivered by $^{188}$Re-18B7 mAb to the brain was approximately ⅓ of the activity delivered to the lungs. The lower proportion of radioactivity in brain tissue than lung tissue is consistent with the notion that the blood brain barrier impeded penetration of radiolabeled mAb. However, the radioactivity in brain tissue was sufficiently high to indicate that a significant fraction of radiolabeled antibody penetrated the blood brain barrier to deliver the fungicidal dose to the CN cells in the brain.

TABLE 1

Induction of apoptosis in *Cryptococcus neoformans* (CN) and *Histoplasma capsulatum* (HC) cells by RIT and gamma radiation

| Fungus | Radiation type | Cellular absorbed dose | Apoptotic cells, % |
|---|---|---|---|
| CN | — | 0 | 3.8 |
| CN | Gamma-rays | 100 krad (1000 Gy) | 13 |
| CN | Gamma-rays | 200 krad (2000 Gy) | 24 |
| CN | Gamma-rays | 400 krad (4000 Gy) | 37 |
| CN | — | 0 | 19 |
| CN | Beta particles $^{188}$Re-18B7, 32 μCi (1184 kBq) | 1.8 krad (18 Gy) | 43 |
| CN | Alpha particles $^{213}$Bi-18B7, 3.2 μCi (118 kBq) | 1.2 krad (12 Gy) | 81 |
| HC | — | 0 | 12 |
| HC | Gamma rays | 400 krad (4000 Gy) | 18 |
| HC | — | 0 | 14 |
| HC | Beta particles $^{188}$Re-9C7, 32 μCi (1184 kBq) | 8.4 krad (84 Gy) | 41 |

*CN cultures were grown for 5 days before treatment, HC - for 7 days.

TABLE 2

Biodistribution of IV injected $^{99m}$Tc-18B7 antibody at 24 h time post-injection in intratracheally infected with CN and healthy BALB/c mice[A]

| | Animals | | |
|---|---|---|---|
| Organ | Infected with CN | Infected with CN and pretreated with 1 mg "cold" 18B7 prior to $^{99m}$Tc-18B7 injection | Healthy controls |
| Blood | 12.77(1.22) | 8.25(0.22) | 8.0(0.70) |
| Liver | 8.71(1.22) | 6.71(0.52) | 4.77(0.32) |
| Kidney | 9.88(0.21) | 7.26(0.28) | 4.47(1.31) |
| Spleen | 4.86(0.14) | 2.53(0.54) | 2.56(0.62) |
| Stomach | 2.43(0.08) | 5.39(1.32) | 1.57(0.35) |
| Lungs | 10.27(1.02) | 4.57(0.33) | 4.57(0.59) |

[A]Results were obtained from n = 3 animals per time point and tabulated as % ID/g (SD)

TABLE 3

Log rank analysis of survival (P values) in CN-infected A/JCr mice, treated 24 h post-infection with $^{188}$Re- and $^{213}$Bi-labeled CN-specific mAb 18B7[A]

| | | Control groups | |
|---|---|---|---|
| Treatment | PBS | $^{213}$Bi ($^{188}$Re)-MOPC21, 100 μCi | "cold"18B7, 50 μg |
| $^{213}$Bi-CHXA"-18B7, 50 μCi | 0.080 | 0.020 | 0.090 |
| $^{213}$Bi-CHXA"-18B7, 100 μCi | 0.009 | 0.001 | 0.002 |
| $^{213}$Bi-CHXA"-18B7, 200 μCi | 0.480 | 0.150 | 0.210 |
| $^{188}$Re-18B7, 50 μCi | 0.005 | 0.009 | 0.015 |
| $^{188}$Re-18B7, 100 μCi | 0.0003 | 0.001 | 0.002 |
| $^{188}$Re-18B7, 200 μCi | 0.080 | 0.046 | 0.057 |

[A]Radiolabeled preparations of 18B7 and of irrelevant control MOPC21 mAbs contained 30-50 μg of "cold" antibody.

TABLE 4

CN CFUs in the lungs and the brains of A/JCr mice infected IV with $10^5$ CN organisms and treated with $^{188}$Re-18B7 mAb 24 h after infection[A]

| Organ | untreated mice and treated with unlabeled 18B7, 50 μg | No. of CFUs/g tissue $(10^4)^B$ | | |
|---|---|---|---|---|
| | | 50 μCi $^{188}$Re-18B7 | 100 μCi $^{188}$Re-18B7 | 200 μCi $^{188}$Re-18B7 |
| Lungs | 550 ± 47 | 11 ± 6 (P = 0.001) | 21 ± 5 (P = 0.001) | 3.3 ± 2 (P = 0.001) |
| Brains | 11 ± 5 | 0.10 ± 0.05 (P < 0.001) | 0.8 ± 0.1 (P = 0.002) | 1.1 ± 0.1 (P = 0.002) |

[A]Animals were sacrificed 48 h after the treatment with $^{188}$Re-18B7 (2.8 $^{188}$Re half-lives); the colony counts are given for 100 and 10 times dilutions for the lungs and brains, respectively.

Example II

Radioimmunotherapy of Pneumococcal Infection

Materials and Methods

Bacteria. *Streptococcus pneumoniae* (Pn) serotype 8 (strain 6308, ATCC) and serotype 3 (strain 10813, ATCC) were grown in tryptic soy broth (TSB) to mid-log phase at 37% in 5% $CO_2$, frozen in TSB in 10% glycerol, and stored at −80° C. Bacteria were taken from frozen stock, streaked on a blood agar plate, and passaged once in TSB before use.

Antibodies. Human mAb D11 (IgM) which binds to PPS 8 which was originally generated from the peripheral lymphocytes of a Pneumovax recipient was produced as in (77). Commercial human myeloma IgM (Calbiochem, Calif.) was used as isotype-matching control.

Radioisotope production and radiolabeling of antibodies. 225-Actinium for construction of $^{225}$Ac/$^{213}$Bi generator was obtained from the Institute for Transuranium Elements, Heidelberg, Germany. $^{225}$Ac/$^{213}$Bi generator was constructed using MP-50 cation exchange resin and $^{213}$Bi eluted with 0.15 M HI (hydroiodic acid) in form of $^{213}$BiI$_5^{2-}$ as described in (15). For radiolabeling with $^{213}$Bi, antibodies were first conjugated to the bifunctional chelating agent CHXA" (N-[2-amino-3-(p-isothiocyanatophenyl)propyl]-trans-cyclohexane-1,2-diamine-N,N',N",N''',N''''-pentaacetic acid) which was a generous gift from Dr. M. Brechbiel (NCI, NIH) as in (16, 75). The average final number of chelates per antibody molecule was determined by the Yttrium-Arsenazo III spectrophotometric method (14). CHXA"-mAb's were radiolabeled with $^{213}$Bi as described in (15).

Immunoreactivity of radiolabeled D11. Immunoreactivity of radiolabeled CHXA"-D11 in comparison with unmodified D11 was determined by evaluating its binding to solid phase PPS8 in ELISA which was performed according to (77). The starting concentration of unmodified D11 and control IgM was 10 μg/mL, and of CHXA"-D11 −2.5 μg/mL.

In vitro activity of labeled Ab against Pn. Approximately $10^7$ cells Pn cells of the serotype 8 strain were placed in microcentrifuge tubes in 50 μL PBS. 213-Bi-D11 mAb in 0.5 mL PBS was added to obtain the desired concentrations of radioactivity per sample (0-4 μCi) with the total amount of mAb per sample being kept constant at 20 μg. After 30 min incubation at 37° C., the cells were collected by centrifugation, the pellets were washed with PBS, diluted, and approximately 1,000 cells were plated on blood agar plates to determine CFU's. To account for non-specific cell killing, Pn cells of the serotype 3 strain to which D11 mAb does not bind were treated with 213-Bi—CHXA"-D11 as above. In another series of experiments conducted essentially as above radiolabeled irrelevant control mAb 213-Bi—CHXA"-IgM was used to treat Pn cells of the serotype 8 to account for non-specific cell killing in comparison with 213-Bi—CHXA"-D11 treatment.

In vivo RIT of Pn infection. The efficacy of RIT against experimental Pn infection was evaluated in mouse strains C57BL/6 and (C57BL/6×129)F$_2$. Mice were infected IP with 1,000 bacteria as measured by CFU. Preliminary experiments were carried out to determine the amount of the mAb that conferred protection against Pn infection in this animal model, by giving the mice (C57BL/6 strain) 1 or 10 μg unlabeled ("cold") D11 P one hour post-infection. One μg/mouse D11 did not confer protection against Pn, while increasing the dose to 10 μg/mouse increased the percentage of mice surviving infection relative to non-treated controls from 30 to 70%. Thus, for RIT of infection in vivo an intermediate amount of 5 μg of mAb D11 per mouse was selected. One hour post-infection the groups of 8-10 animals were treated with 80 μCi 213-Bi—CHXA"-D11 or 213-Bi—CHXA"-IgM (5 μg), 5 μg "cold" D11 or left untreated. The animals were observed for their survival and vital signs for 14 days.

Determination of bacterial load in RIT-treated mice. To determine whether RIT has bacteristatic or bactericidal effect on Pn cells in vivo, we determined the serum bacterial burden. Blood was obtained from the tail veins of 213-Bi—CHXA"-D11-treated mice on Days 3 and 14 post-therapy, and dilutions of the blood in TSB were plated in duplicate on blood agar plates, incubated for 18 h, and the number of CFU's per mL of blood was counted. The limit of detection was 10 CFU's.

Determination of platelet counts. For measurement of platelet counts, blood of C57BL/6 mice used in the therapy studies was collected from the tail vein into heparinized capillary tubes on day 3, 7 and 14 days post-therapy. The background measurement of the platelet counts was obtained for healthy C57BL/6 mice. Four μL of blood was mixed with 2.5 μL 10% EDTA. One μL of the anticoagulated blood was then mixed with 100 μL of 1% ammonium citrate. Platelets were counted in a hemocytometer using phase contrast, at 400 times magnification, as described in (76).

Statistical analysis. Student's t test for unpaired data was employed to analyze differences in the number of CFU'S between differently treated groups during in vitro therapy studies. The log-rank test was utilized to assess the course of animal survival. Differences were considered statistically significant when P values were <0.05.

Results

Radiolabeling of antibodies with 213-Bi. Both D11 mAb and control IgM proved to be amenable to conjugation with CHXA" ligand with average final number of chelates per antibody molecule ranging from 1.5 to 3.0 as determined by the Yttrium-Arsenazo III spectrophotometric method. The radiolabeling of CHXA"-mAb conjugates resulted in 95±3% yields.

Figure 7:
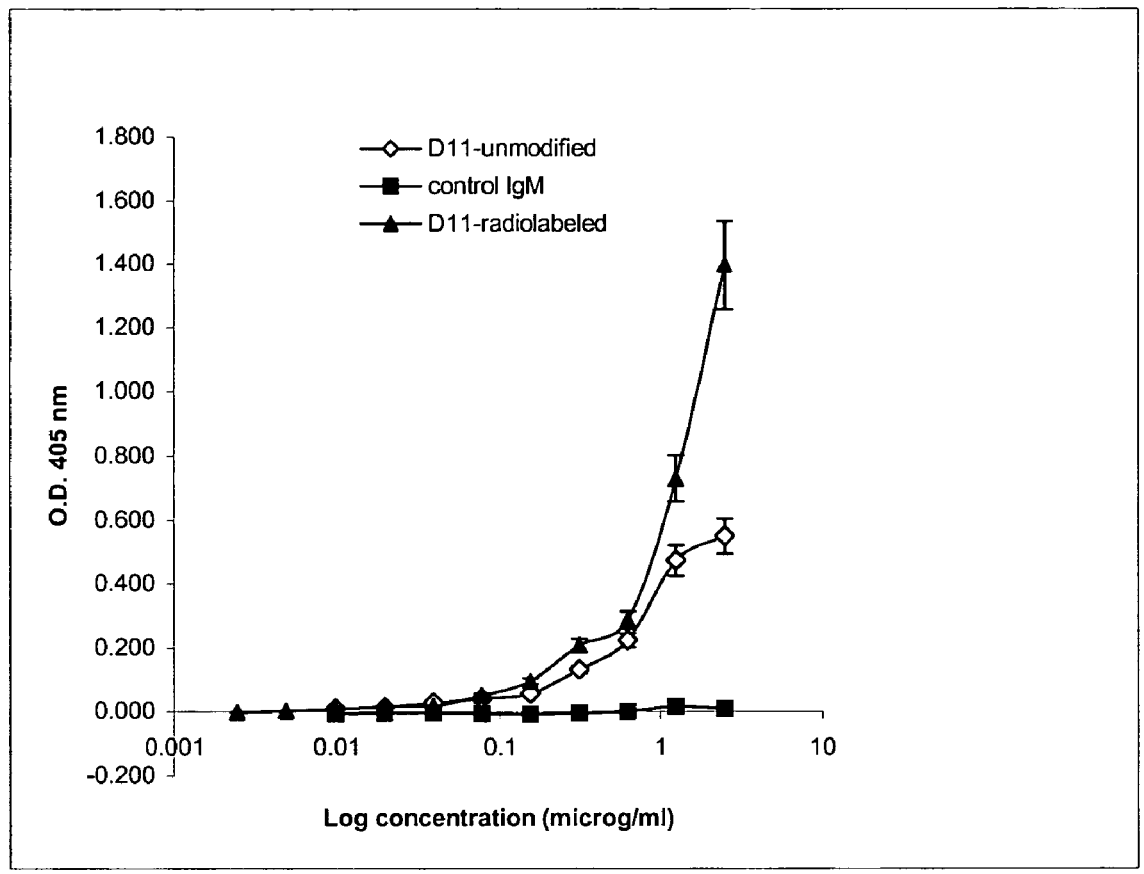
FIG. 7. Immunoreactivity of radiolabeled D11 antibody by ELISA

Immunoreactivity of radiolabeled 213-Bi—CHXA"-D11 mAb. The results of 213-Bi—CHXA"-D11 (referred further in the text as 213-Bi-D11) binding to solid PPS8 are presented in FIG. 7. Attachment of CHXA" ligand followed by radiolabeling with 213-Bi did not compromise the immunoreactivity of D11 mAb. These results established the feasibility of radiolabeling mAb D11 while retaining its ability to bind to PPS8.

Figures 8A, 8B:
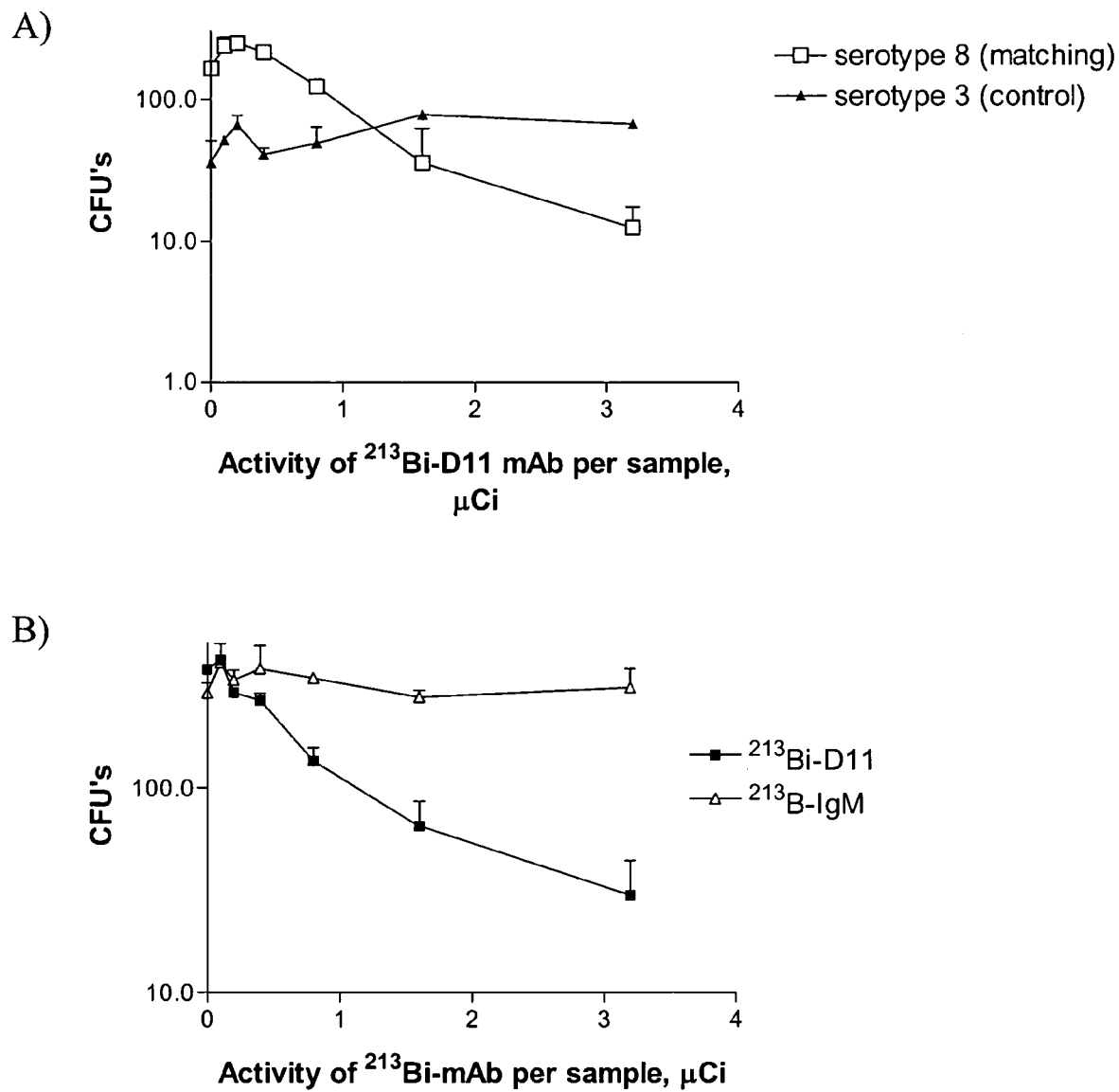
FIGS. 8A-8B. RIT of *Streptococcus pneumoniae* (Pn) with PPS 8-specific $^{213}$Bi-D11 mAb in vitro. A) serotype 8 and serotype 3 (control); Pn strains were treated with the same activities of 213-Bi-D11 mAb. B) serotype 8 Pn was treated with the same activities of 213-Bi-D11 and 213-Bi—IgM (control) mAbs. Amount of mAb per sample was kept constant at 20 µg. Each experiment was performed in duplicate. Error bars represent SD.

Activity of radiolabed mAb against Pn in vitro. In vitro therapy of Pn was performed with radiolabeled 213-Bi-D11 in order to evaluate the susceptibility of Pn towards 213-Bi alpha-particles delivered by Pn-specific antibody. FIG. 8(A) shows the results of in vitro RIT of Pn serotype 8 with PPS8-specific 213-Bi-D11 mAb and of Pn serotype 3 which does not bind D11 mAb. Incubation of serotype 8 Pn with 213-Bi-D11 resulted in dose dependent killing of bacteria. In contrast, incubation of Pn serotype 3 with 213-Bi-D11 with the same specific activity produced only minimal killing within the investigated range of activities (P=0.001). In another series of experiments, the ability of 213-Bi-D11 to eradicate Pn serotype 8 was compared to the effect of 213-Bi—IgM irrelevant control mAb used in the same range of activities. No killing of Pn with 213-Bi—IgM was observed. The significantly higher killing associated with the specific antibody almost certainly reflects higher radiation exposure for Pn as a consequence of antibody binding to the PPS8. The activity of 213-Bi-D11 against Pn in vitro indicated that radiolabeling made the antibody bactericidal.

Figure 9A:
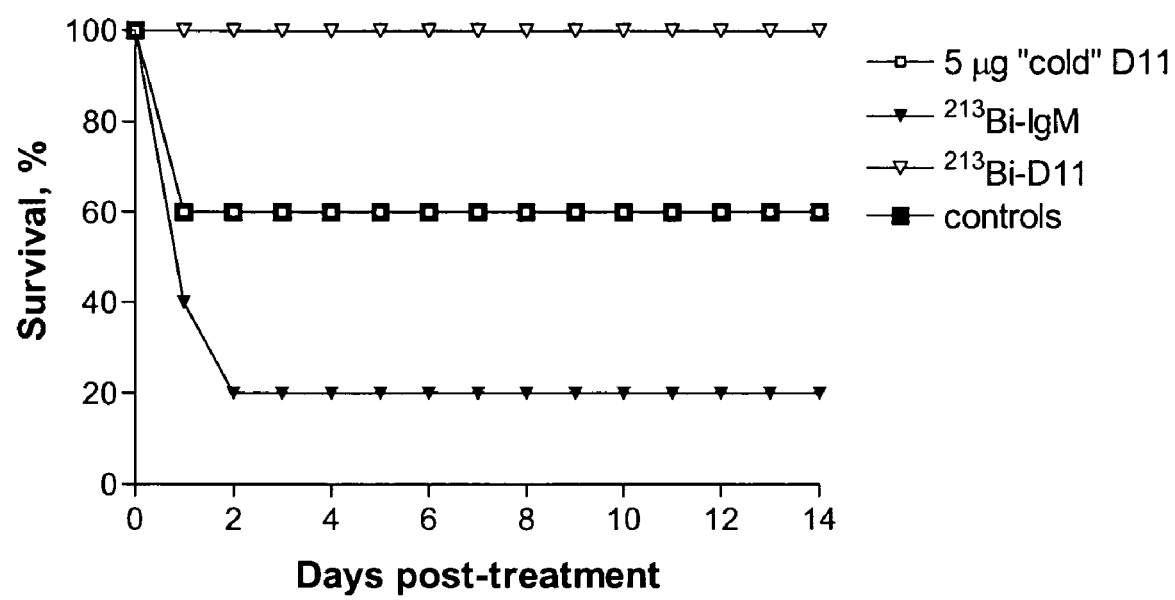
FIGS. 9A-9C. RIT of Pn infection with $^{213}$Bi-labeled mAb's in vivo. A), B) C57BL/6 strain. C) (C57BL/6×129)F$_2$ strain. 8-10 mice were used per group. Mice were infected i.p. with 1,000 organisms 1 h before treatment with mAbs.
Figure 9B:
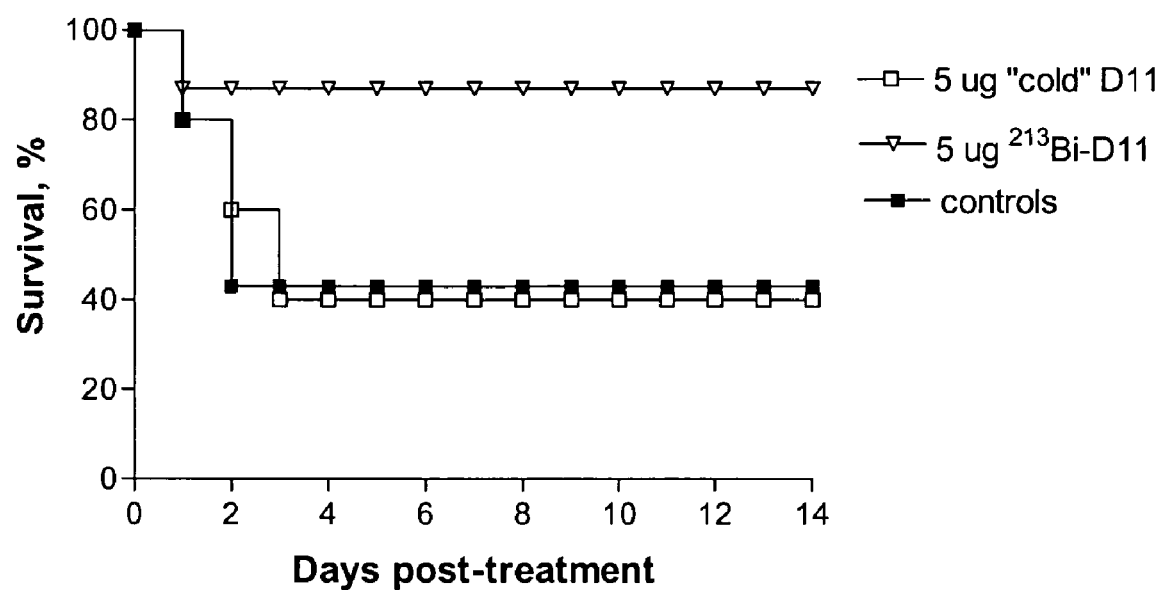
Figure 9C:
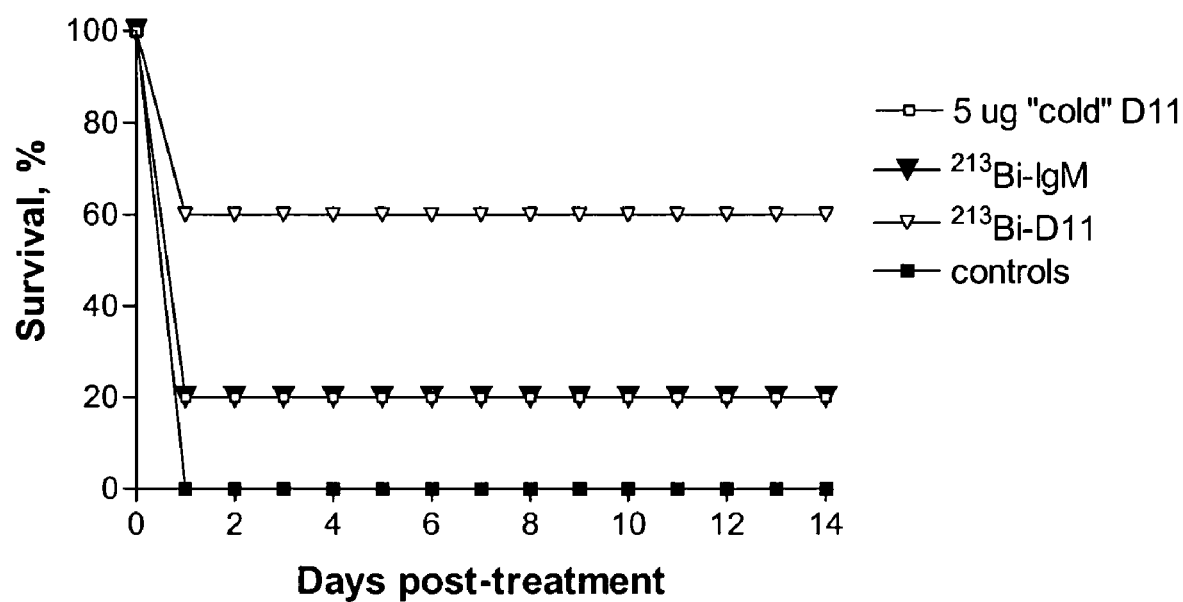

FIGS. 9A-9C shows the RIT results of Pn infection in 2 different mouse strains—C57BL/6 (FIGS. 9A, 9B) and (C57BL/6×129)$F_2$ (FIG. 9C). Pn infection was more aggressive in (C57BL/6×129)$F_2$ strain (b). For both strains a greater percentage of mice survived in the 213-Bi-D11-treated group relative to the control group. Unlabeled D11 in the amount of 5 µg did not confer protection from infection. Radiolabeled control IgM also did not have any therapeutic effect. Mice in control groups succumbed to bacteremia on Day 1-3, while mice treated with 80 µCi 213-Bi-D11 demonstrated 87-100% and 60% survival for strains C57BL/6 and (C57BL/6×129)$F_2$, respectively, and showed no bacteria in their blood as measured by CFU's on Days 3 and 14, proving that radiolabeled D11 mAb has a bactericidal effect on Pn cells. Treatment with radiolabeled D11 was very well tolerated—no weight loss, changes in eating and drinking habits and no other visible signs of radiotoxicity were observed in treated animals.

Figure 10:
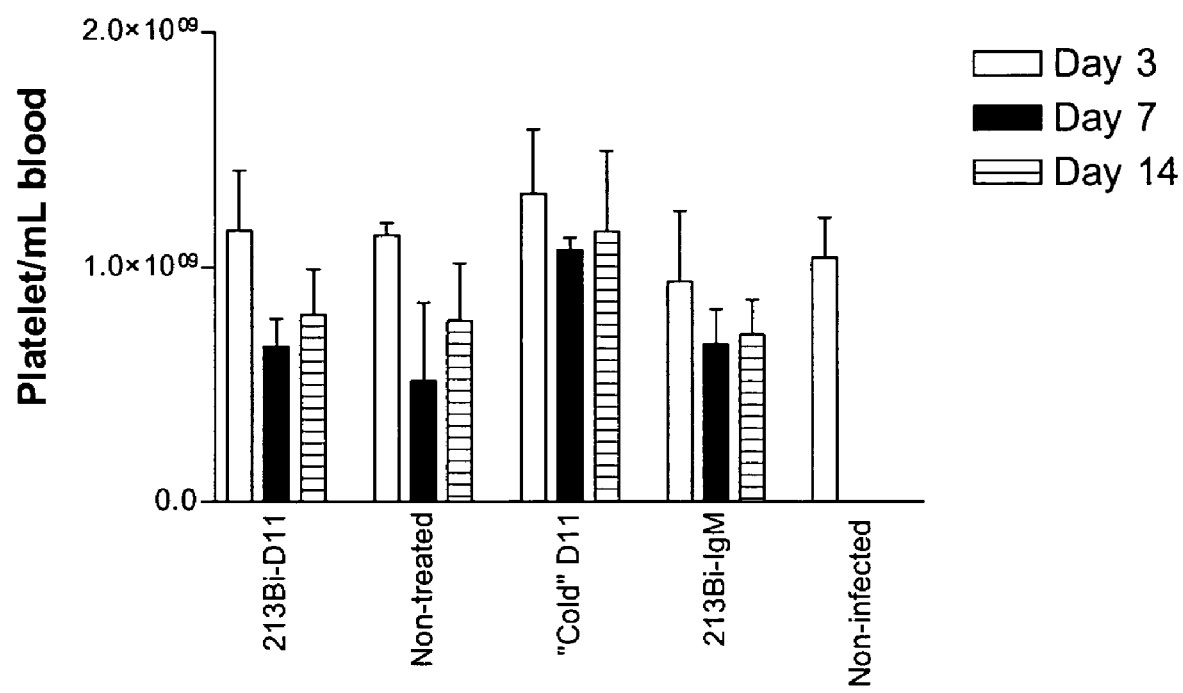
FIG. 10. Platelet counts in C57BL/6 mice infected i.p. with Pn and treated with 213-Bi-labeled mAb's 1 h post-infection.

Toxicity studies. The number of platelets in peripheral blood was determined as a measure of radiation toxicity in Pn-infected C57BL/6 mice treated with 213-Bi-D11 and 213-Bi—IgM mAb's in comparison with mice treated with "cold" D11 and with non-treated infected controls (FIG. 10). It should be noted that platelet counts in 213-Bi—IgM, "cold" D11 and infected non-treated mice were acquired in few surviving animals while the platelet counts in 213-Bi-D11-treated animals were obtained from significantly larger number of animals. There was no statistically significant difference in platelets on Day 3 post-infection in treated or non-treated infected mice in comparison with healthy animals. The drop in platelet count was observed in all groups on Day 7 post-infection, including 213-Bi-D11 group where the counts were significantly different (p=0.01) in comparison with Day 3. This can be explained by the effect of prior Pn infection on platelets as well as by the fact that the nadirs in platelet counts are usually reached at 1 week after radiolabeled antibody administration in RIT of cancer patients (31). On day 14 post-therapy the platelet count in 213-Bi-D11 group went up and there was no difference with the count on Day 3 (p=0.06) which reflects the lack of toxicity of 213-Bi-D11 treatment in C57BL/6 mice. The fact that administration of 80 µCi dose of 213-Bi-D11 proved to be therapeutic and safe in the systemic model of Pn infection is in conformance with the results in Example I where 100 µCi dose of 213-Bi-18B7 mAb was shown to have a therapeutic effect and no short- or long-term toxicity in mice infected systemically with *C. neoformans*.

Example III

Effectiveness of Radioimmunotherapy Using a Plurality of Different Radioisotopes One important factor in determining the choice of a radioisotope for use in RIT is its emission range in tissue. Experiments were conducted to evaluate the efficacy of using a combination of two radioisotopes with different emissions for better targeting and elimination of microbial cells. A combination of the short range alpha-emitter 213-Bi and the long range beta-emitter 188-Re attached to 18B7 mAb was used to treat mice infected with *C. neoformans*. As shown in Table 5, the combination of 213-Bi and 188-Re was more efficient in reducing the fungal load in the lungs of the mice infected with *C. neoformans* than the same activities of either 213-Bi or 188-Re alone.

TABLE 5

CN CFU's in the lungs of A/JCr mice infected IV with $10^5$ CN organisms and treated with $^{188}$Re-18B7 mAb, $^{213}$Bi-18B7 mAb or their mixture 24 h after infection$^A$

| Organ | untreated mice and mice treated with unlabeled 18B7, 50 µg | 100 µCi $^{188}$Re-18B7 | 100 µCi $^{213}$Bi-18B7 | 50 µCi $^{213}$Bi-18B7 + 50 µCi $^{188}$Re-18B7 |
|---|---|---|---|---|
| | | Number of CFU's/g tissue, × $10^4$ (SD) | | |
| Lungs | 600(50)$^B$ | 25(6) (P = 0.001) | 10(5) (P = 0.001) | 2.5(2) (P = 0.001) |

$^A$Animals were sacrificed 48 h after the treatment; the colony counts for 100 dilution for the lungs are given. $^B$P values were calculated by the Wilcoxon test, the groups treated with radiolabeled mAb were compared to combined group of untreated mice and treated with unlabeled 18B7 mAb.

Example IV

Production of Monoclonal Antibodies Against Microbial Antigen by Hybridoma Technology If an antibody is not available for any particular microorganism or parasite, it can be readily generated without undue experimentation using the following standard protocol.

Method of immunization. Mice will be immunized with purified organism-specific antigen by several methods to determine the most active route of vaccination. The antigen will be used with or without adjuvant. Freund's complete adjuvant for initial immunization followed by Freund's incomplete adjuvant will be used. CpG (unmethylated cytosine-guanine dinucleotides) has been shown to be a highly effective (enhances T cell help) and safe immunogen (46, 47). CpG will be used according to the manufacturer's recommendations (ImmunoEasy Mouse Adjuvant, Qiagen). Bacterial DNA contains high amounts of CpG motifs. The vertebrate immune system has apparently evolved to recognize these CpG motifs as foreign, resulting in a Th1-biased immune response (46). The efficacy may differ between mice immunized with Freund's compared to CpG, since Freund's is often associated with a Th2 directed response and CpG either a mixed Th1/Th2 or a strong Th1 response (47). Both intraperitoneal and base of tail routes will be assessed. Although the intraperitoneal approach was used in the immunizations that identified mAb 6D2 to C. neoformans melanin (48), the base of tail route appears to be more effective since the lymph nodes in this region drain directly into peritoneal lymph nodes rich in dendritic cells, which are considered to be the first line of antigen presentation (49). Serum will be obtained prior to immunization and at various times following immunization. Effectiveness of immunization will be determined by incubation of serially diluted serum in 96 well plates coated with antigen that has been blocked for non-specific binding. Following incubation of the serum, the wells will be washed and alkaline phosphatase (AP)-labeled goat anti-mouse (GAM) IgG/M will be applied. The reaction will be developed with p-nitrophenyl phosphate substrate (p-NPP) and measured at an OD of 405 nm. Pre-immune serum will be compared to serum obtained after immunization for each mouse. The isotype response to immunization will be characterized using the ELISA with specific immunoglobulin isotypes.

Generation of mAbs. Splenocytes from mice with strong antibody responses to immunization will be fused with non-producing myeloma partners (48). Hybridomas will be generated by a fusion of spleen cells to myeloma cells at a 4:1 ratio in the presence of 50% polyethyleneglycol. The cell mixture will be suspended in a defined complete hypoxanthine-amionpterin-thymidine (HAT) media, with L-glutamine containing 20% heat-inactivated fetal bovine serum, 10% NCTC-109, HAT, and 1% nonessential amino acids for selection of hybridomas, plated in 96-well tissue culture plates, and incubated in a 10% $CO_2$ incubator at 37° C. Screening of the hybridomas for the presence of mAbs to antigen will be performed by incubation of supernatants in 96 well plates coated with antigen then blocked to prevent non-specific binding. The wells will be washed and AP-labeled (GAM) IgG/M will be applied. The reaction will be developed with p-NPP and measured at an OD of 405 nm. The isotypes of the mAbs will be characterized. Large concentrations of mAb will be generated by making ascites in SCID mice or from supernatant generated from the selected hybridomas. The mAb in supernatant can be purified by a column of agarose beads labeled with Ab to the appropriate mouse immunoglobulin (Sigma), and concentrated by centrifugation in an 100,000 NMWL ultrafree®-15 centrifugal filter device (Millipore).

Labeling antibodies with radioisotopes. The antibodies can be radiolabeled with any radioisotopes using one of two techniques—"direct" radiolabeling (17) or radiolabeling through bifunctional chelating agent (50).

Example V

Generation of Peptides Which Bind Specifically to an Agent Causing Infection

Phage display is a powerful technique to identify peptides that bind to specific antigens. Phage display was used to identify *C. neoformans* melanin-binding peptides (81). Identified microbial antigens will be screened with phage display libraries (82, 83) and the binding phage will be purified. The antigen-binding phage will be selected as described (81). Briefly, the antigen will be collected by centrifugation and washed to remove non-binding phage. Bound phage will be eluted by acid, amplified in bacteria, and purified. The selected phage will undergo repeated rounds of screening with antigen to isolate highly specific binders. After each screen, the proportion of antigen-specific phage will be compared to the number of phage used for the screen. When there is no further enrichment (usually by 4 rounds of screening), sequences of peptides displayed in the selected phage will be determined using established primers (81). The sequences will provide information about the molecular characteristics of the epitope. Reactivity of the phage with antigen can be determined by ELISA by capturing the phage with an antibody to the phage protein (81). Negative controls will use a phage lacking the insert (82) or phage containing non-specific inserts (83). The sequenced peptides are synthesized by solid state peptide synthesis with or without incorporation of ligands capable of binding radionuclides.

Discussion

At the beginning of the 21st century the field of infectious diseases is facing significant challenges. There is an increasing prevalence of infections with highly resistant microorganisms that are not susceptible to existing antimicrobial agents. Medical progress and the HIV epidemic have produced large numbers of immunosuppressed individuals who are susceptible to many unusual pathogens and in whom standard antimicrobial therapy is often not very effective. New pathogens have emerged, many of which are not susceptible to existing therapies. These problems are complicated by a relative paucity of new drugs as evidence by the dearth of new antibiotic classes introduced in the past decade (26). Furthermore, the specter of biological warfare has raised a new dimension of threat to humanity from infectious diseases. Certainly, the relative ease by which certain biological agents can be engineered for drug and/or vaccine resistance raises concerns about the adequacy of existing antimicrobial strategies in protection against biological warfare. Hence, the current climate suggests an urgent need for new approaches to antimicrobial therapy. Unfortunately, there have been no new antimicrobial strategies that directly target pathogens since the concept of chemotherapy was proven by the introduction of sulfonamide in 1935.

The present application discloses the efficacy of radioimmunotherapy (RIT) in treating infections using as examples: the monoclonal antibody 18B7 to the *C. neoformans* capsule radiolabeled with $^{188}$Re or $^{213}$Bi for treatment of CN infection in vitro and in vivo, the monoclonal antibody 9C7 to a protein antigen on the surface of the *H. capsulatum* cell wall radiolabeled with $^{188}$Re for treatment of HC infection in vitro, the human monoclonal antibody D11 to pneumococcal capsular polysaccharide 8 radiolabeled with $^{213}$Bi for treatment of *Streptococcus pneumoniae* infection in vitro and in vivo, and 18B7 radiolabeled with a mixture of $^{188}$Re and $^{213}$Bi for treatment of CN infection in vivo. Prior to the subject invention, it was not apparent that the radiolabeled antibodies would be stable in vivo since anti-Cryptococccus antibodies radiolabeled with 125-Iodine quickly lose their radiolabel in vivo (53). It was also not apparent beforehand that the radiolabeled antibodies could deliver lethal doses to pathogens, as the percentage binding to the pathogens could have been too low to deliver lethal doses. Also, it was not apparent that the pathogens would be susceptible to particulate radiation since certain types of microorganisms (i.e., bacterium *Deinococcus radiodurans*, and yeasts *Cryptococcus neoformans, Saccharomyces ellipsoideus* and *Saccharomyces cerevisiae*) are extremely resistant to gamma radiation. It takes on average 10-1000 times higher radiation dose to kill microorganisms than mammalian cells (2, 54-56). Furthermore, the present application discloses the surprising and important finding that radioimmunotherapy of infections with a combination of different radioisotopes is more effective than RIT using a single radioisotope. The advantageous efficacy of treating infections with such combined radioimmunotherapy had not previously been apparent.

Comparing the response of CN and HC fungi to gamma radiation and RIT with $^{188}$Re- and $^{213}$Bi-labeled antibodies revealed that RIT with organism-specific radiolabeled antibodies (FIGS. 5A-5B) were significantly more efficient than external gamma radiation (FIGS. 2A-2B). The radiation doses required to kill CN fungal cells were 1000-fold lower when delivered by radiolabeled antibodies compared to gamma radiation and, the alpha emitter $^{213}$Bi was about two times more lethal than the beta emitter $^{188}$Re. Furthermore, the dose rates delivered by the radiolabeled antibodies were thousands of times lower than those delivered acutely with the external gamma radiation (30 Gy/min). This is consistent with clinical RIT where peak dose rates of 10 rad/h (0.1 Gy/h) (67) are observed. For comparison, high-dose rate radiation, which is typical for external beam radiation therapy, delivers 6000 rad/h (60 Gy/h). Thus, from the viewpoint of radiation therapy, RIT delivers suboptimal dose rates to tumors (or to microbial cells in the present case).

Targeted radionuclide therapy can be effective against infections even at suboptimal doses through mechanisms such as the induction of apoptosis in irradiated cells, "bystander" effect (death of adjacent, non-irradiated cells) and cell cycle arrest (67-70). The flow cytometry results in Table 1 indicate that low doses of particulate radiation delivered by organism-specific antibody caused the majority of treated cells to die apoptotic death while much higher doses of gamma radiation induced apoptosis only in ~30% of irradiated cells. The surprising efficacy of RIT could reflect the occurrence of a different cascade of events resulting from the interaction of the electrons and alpha particles (emitted by radiolabeled antibodies on the cell surface) with the cell membrane itself or with structures within the cell. In fact, there is evidence to suggest that cellular radioactivity can cause uniquely different gene expression profiles than external gamma rays (71). Alternatively, it is conceivable that antibody molecules also mediate local effects that enhance the microbicidal efficacy of radiation. In this regard, antibody molecules have recently been shown to be catalysts for the production of microbicidal oxygen-related oxidants (72). Hence, particulate radiation combined with local production of toxic oxidative molecules could result in synergistic antimicrobial effects that translate into significantly greater efficacy for RIT than would be expected from dosimetry calculations alone.

Figure 5C:
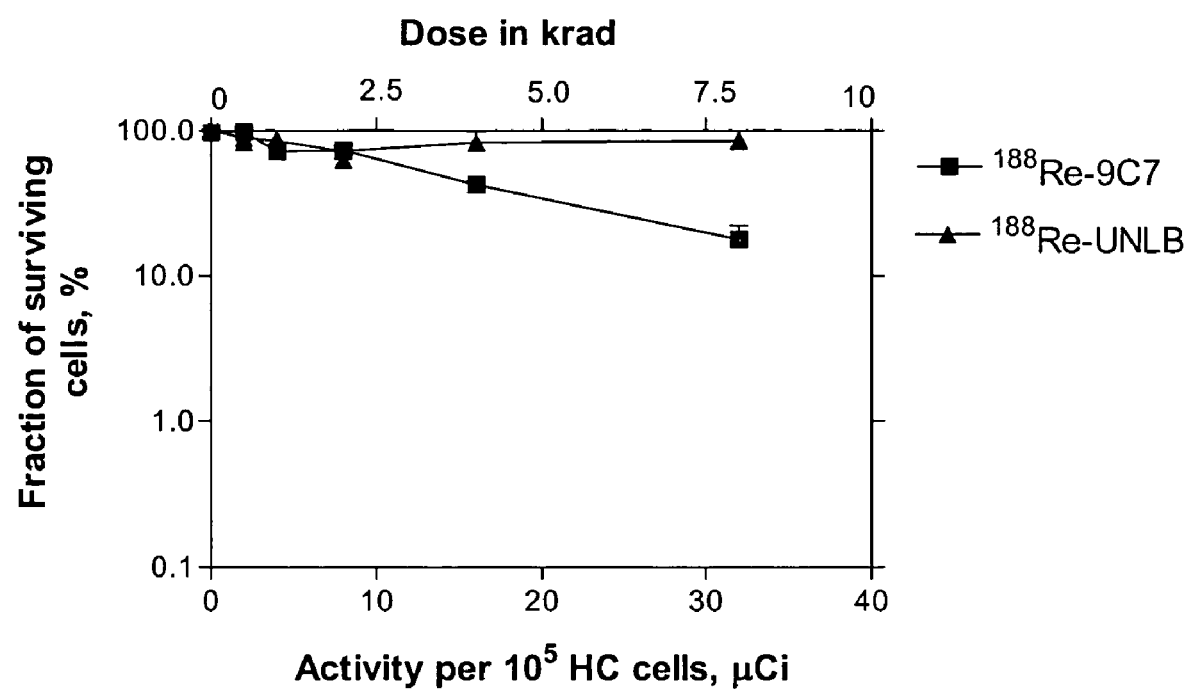

Despite the fact that HC and CN responded similarly to external gamma radiation (FIGS. 2A-2B), HC was less susceptible to RIT with $^{188}$Re-labeled organism specific antibody than CN (FIGS. 5A, 5C). A cellular absorbed dose of about 8 krad (80 Gy) was required to eradicate 80% of HC cells (FIG. 5C) whereas less than 1 Gy was required to eradicate a similar fraction of CN cells (FIG. 5A). The differences in calculated cellular absorbed doses is, in part, attributed to their very different cell diameters (5 µm for HC and 10 µm for CN), which in turn affects their mean absorbed dose per decay (S value). While the cellular absorbed doses required to eradicate a specific fraction of cells may be quite different, it is possible that the local absorbed doses on the cellular membrane are more similar. Another factor that may be involved in the observed differences in responses is a lower density of antibody molecules on the surface of HC cells relative to CN cells. For CN~$10^8$ antibody molecules were bound to each cell whereas for HC only 2×$10^7$ antibody molecules were bound to each cell. Furthermore, the fact that the mAbs used in CN and HC RIT are of IgG1 and IgM isotypes, respectively, could suggest that isotype related effects contribute to the lethality of RIT. Nevertheless, regardless of the mechanisms involved, the cellular absorbed dose of 8 krad (80 Gy) delivered by $^{188}$Re-9C7 mAb was almost 100 times lower than the dose of gamma radiation needed to cause comparable killing of HC cells (FIGS. 2B and 5C). The killing was antibody-specific since incubation of HC with radiolabeled control antibody resulted in only negligible killing of HC cells.

RIT with *Streptococcus pneumoniae* (Pn)—specific mAb radiolabeled with alpha-emitting radioisotope 213-Bi proved to be an efficient and safe treatment modality in two different mouse strains. In contrast to fungal infections which are usually chronic, bacterial infections tend to progress more rapidly and bacteria replicate at considerably faster rate than fungi. For example, the replication rate of Pn and *C. neoformans* are 20 min and 3 h, respectively. Cryptococci have average volumes that are approximately 100× larger than pneumococci and present significantly larger targets for RIT. It remains to be seen if the sensitivity of a microorganism towards particulate radiation depends on the amount of DNA per volume matter. In addition, these two microbes elicit different inflammatory responses with neutrophils predominating in pneumococcal infections and macrophages predominating in cryptococcal infections. Consequently, the success of RIT against experimental cryptococcal infection could not be extrapolated a priori to bacteria.

There are several factors which make Pn potentially more amenable to RIT in vitro and in animal models than fungal infections. First, bacteria are known to be at least one order of magnitude more radiosensitive to external radiation than fungi (1). In spite of their extreme radioresistance to external radiation it is possible to achieve significant killing of pathogenic fungi *C. neoformans* and *H. capsulatum* with specific radiolabeled antibodies both in vitro and in vivo. Thus, inherent radiosensitivity of bacteria may translate into better therapeutic outcomes for RIT. The complete absence of Pn cells in the blood of RIT-treated mice attests to full eradication of infection by targeted radiation.

In regards to the radiosensitivity of parasites and viruses to external radiation, doses of 60,000 rad external radiation are lethal to some parasites (84). Thus, parasites are ~10 times more radiosensitive to external radiation than fungi and probably are close to bacteria in their radiosensitivity. Viruses, however, have the same or ~1.5 times higher radioresistance than fungi with the doses over 1,000,000 rad external radiation needed for significant viral killing (85).

The high-energy β-emitter 188-Rhenium ($^{188}$Re) and α-particle emitter 213-bismuth ($^{213}$Bi) were used herein as therapeutic radionuclides for RIT of infection. $^{188}$Re ($T_{1/2}=$ 16.7 h) is a high-energy β-emitter ($E_{max}$=2.12 MeV) that has recently emerged as an attractive therapeutic radionuclide in diverse therapeutic trials including cancer radioimmunotherapy, palliation of skeletal bone pain, and endovascular brachytherapy to prevent restenosis after angioplasty (27-29). $^{188}$Re has the additional advantage that it emits γ-rays which can be used for imaging studies. $^{213}$Bi ($T_{1/2}$=45.6 min) emits a high linear energy transfer (LET) α-particle with E=5.9 MeV with a path length in tissue of 50-80 μm. Theoretically a cell can be killed with one or two α-particle hits. $^{213}$Bi was proposed for use in single-cell disorders and some solid cancers (20, 30-32) and has been used to treat patients with leukemia in Phase I clinical trials (33, 34). $^{213}$Bi is the only α-emitter that is currently available in generator form, which allows transportation of this isotope from the source to the clinical centers.

The present results indicate that antibodies labeled with $^{188}$Re or $^{213}$Bi were effective in vitro and therapeutic in vivo as demonstrated by significant prolongation of survival of lethally infected mice. Prior to the subject invention, the suitability of using the alpha-emitting radioisotope (213-Bismuth) or strong beta-emitting radioisotope (188-Rhenium) for treatment of systemic infection was not obvious since the tissue range of their emissions could have been too short or too long to kill the pathogen. The reduction in organ CFUs observed for mice given RIT indicates that the prolongation of survival is likely a result of reduced organ fungal burden as a consequence of direct microbicidal activity by radiolabeled antibody in vivo. The observation that RIT-treated mice had lower CFUs in brain tissue indicates the ability of radiolabeled antibody to penetrate this organ despite the blood-brain barrier. This phenomenon may reflect the increased permeability of the blood-brain barrier that has been reported in experimental cryptococcal meningitis (35).

In the clinical setting patients with established cryptococcosis have large amounts of circulating capsular polysaccharide (cryptococcal antigen) that could interfere with RIT by binding radiolabeled mAb. There are three options to circumvent this potential problem if RIT is to be used clinically for treatment of cryptococcosis. First, one could administer "cold" antibody in sufficient amount to clear serum antigen. The ability of antibody to clear serum antigen has been demonstrated in humans with cryptococcosis treated with small amounts of rabbit immune serum (36). Second, one could use a variation of this approach, called the "pre-targeting" technique which is based on avidin-biotin interaction, and which has been used successfully in patients with high-grade glioma and other cancers in which soluble antigen interferes with tumor targeting (37). This procedure involves the use of a biotinalated "cold" antibody to bind to CN at the infection sites and to the antigen in the blood. This step is called "pre-targeting". During the next step avidin is given to bind the biotin on the antibody and the biotin on the antibody-antigen complex thus helping to clear it from the blood. This is a "clearance" step. Finally, there is a "targeting" step when the radioactivity is injected into the patient in the form of small molecular weight radiolabeled biotin which quickly binds to the avidin on the antibody already attached to CN at the sites of infection. Such regiments, of course, would require fine-tuning of the amounts of antibody and radiolabeled biotin given and times between the steps.

The third approach would be to defer the use of RIT until standard antifungal therapy reduces serum antigen levels to very low levels. Currently there are two major problems in the therapy of cryptococcosis: 1) an unacceptable high level of early mortality caused by brain edema that is probably polysaccharide related; and 2) an unacceptable high level of recurrences after antifungal therapy is discontinued. RIT may be most useful for eradicating remaining foci of infection, such as those reported in the prostate which are believed to contribute to relapsed disease (38). Furthermore, the problems specific to cryptococcosis are unlikely to arise if RIT is applied to other infectious diseases that are not accompanied by high serum antigen load.

Passive antibody therapy was the first effective antimicrobial therapy and remains a potentially useful strategy against a variety of infectious diseases (39). However, naked antibody therapies have certain inherent limitations that have precluded their use except for a limited number of diseases. Another advantage of RIT relative to naked antibody therapy is that the latter can be complicated by the occurrence of prozone-like effects at high antibody concentrations (45). Since the killing power of RIT is based on radiation, prozone-like phenomena are not expected to occur. However, antibodies provide attractive vehicles for the delivery of microbicidal agents as a result of the specificity of the antigen-antibody interaction.

Certain features of infection make it more amenable than cancer for treatment with RIT. Tumors are more difficult to target with specific antibodies than microorganisms because tumors present great antigenic variability, and often express antigens (such as CEA—carcinoembrionic antigen) that are also found on normal tissue, thus making treatment less specific. Solid tumors present other challenges such as slow penetration rate of antibodies into tumor tissue and hypoxia, which decreased the efficiency of treatment with β-emitting radioisotopes. In contrast, pathogen-specific antibodies are likely to reach the infectious foci quickly given that increased capillary permeability at the sites of infection allows radiopharmaceuticals to easily migrate from the circulation (44). Also, in contrast to cancer therapy, where a single surviving cell can lead to tumor recurrence, in most infectious diseases it is not necessary for the treatment to kill every microbe to achieve a therapeutic benefit since the immune system may effectively control infection when the inoculum is reduced by microbicidal radiation. For treatment of infection within abscesses or in the difficult to access sites deep in the body, longer-lived isotopes such as 90-Yttrium (half-life 2.7d), 177-Lutetium (half-life 6.7 d) or 131-Iodine (half-life 8 d) can be used.

The data accumulated in clinical RIT of cancer indicate that the primary toxicity of high-dose RIT of infection is likely to be bone marrow suppression. Important determinants of the extent and duration of myelosuppression include bone marrow reserve (based on prior cytotoxic therapy and extent of disease involvement), total tumor (infection) burden, spleen size and radioimmunoconjugate stability (41). The potential routes to circumvent this problem may include fractionated RIT, use of hematologic support, and "chasing" of the excess of radiolabeled antibody with clearing reagents (41). Also, given the short trajectory of the particle it is likely that most hits would occur on pathogens or immune cells in the immediate vicinity. Presumably as pathogens are killed, other immune effector cells that are recruited will be more effective in clearing up the site.

The present study demonstrates that RIT can be used as an effective anti-infective modality. RIT may be of particular value alone or in combination with standard therapy for the treatment of infections 1) in special populations such as immunosuppressed patients infected with CN or with other AIDS-associated opportunistic infections, 2) due to highly resistant microorganisms for which therapeutic options are currently very limited, and 3) for diseases caused by microbes for which there is no effective antimicrobial chemotherapy. This method is believed to be suitable for use against a variety of infectious diseases including such difficult to treat conditions as Aspergillosis in organ-transplant patients. One attraction of developing RIT for infectious diseases is that it represents the "marriage" of two mature technologies, monoclonal antibodies and nuclear medicine, in a novel application where the limitations encountered in using this approach for tumor therapy are much less confining. Development of RIT for certain types of infections represents the first new antimicrobial therapy since the introduction of antibiotics over a half-century ago.

REFERENCES

1. Casarett, A. P. 1968. *Radiation Biology*. Prentice-Hall, NJ, USA. 367 pp.
2. Dembitzer, H. M., Buza, I., Reiss, F. 1972. Biological and electron microscopic changes in gamma radiated *Cryptococcus neoformans*. *Mycopathol. Mycol. Appl.* 47: 307-315.
3. Zack, M. B., Stottemier, K., Berg, G., and Kazemi, H. 1974. The effect of radiation on microbiologic characteristics of *M. tuberculosis*. *Chest* 66: 240-243.
4. Dadachova, E. 1999. Preparation of $^{198}$Au(I)-labelled gold-chloroquine complex [$^{198}$Au(PPh$_3$)(CQ)]PF$_6$ as a potential antimalarial agent. *J. Label. Comp. Radiopharm.* 42: 287-292.
5. Goldenberg, D. M., Sharkey, R. M., Udem, S., Vagg, R., Levine, G. M., Conte, P., Swayne, L. C., Hansen, H. J., Cunniff, D., Anton, J. et al. 1994. Immunoscintigraphy of *Pneumocystis carinii* pneumonia in AIDS patients. *J. Nucl. Med.* 35: 1028-1034.
6. Malpani, B. L., Kadival, G. V. and Samuel, A. M. 1992. Radioimmunoscintigraphic approach for the in vivo detection of tuberculomas—a preliminary study in a rabbit model. *Nucl. Med. Biol.* 19: 45-53.
7. Casadevall, A. and Pirofski, L. 2001. Adjunctive immune therapy for fungal infections. *Clin. Infect. Dis.* 33: 1048-1056.
8. Spitzer, E. D., Spitzer, S. G., Freundlich, L. F., and Casadevall, A. 1993. Persistence of the initial infection in recurrent cryptococcal meningitis. *Lancet* 341: 595-596.
9. Currie, B. P., and Casadevall, A. 1994. Estimation of the prevalence of cryptococcal infection among HIV-infected individuals in New York City. *Clin. Infect. Dis.* 19: 1029-1033.
10. Lendvai, N., and Casadevall, A. 1999. Monoclonal antibody-mediated toxicity in *Cryptococcus neoformans* infections: mechanism and relationship to antibody isotype. *J. Infect. Dis.* 180: 791-801.
11. Casadevall, A., Mukherjee, J., Devi, S. J., Schneerson, R., Robbins, J. B., and Scharff, M. D. 1992. Antibodies elicited by a *Cryptococcus neoformans*-tetanus toxoid conjugate vaccine have the same specificity as those elicited in infection. *J. Infect. Dis.* 165: 1086-1093.
12. Casadevall, A., Mukherjee, J., and Scharff, M.D. 1992. Monoclonal antibody based ELISAs for cryptococcal polysaccharide. *J. Immunol. Methods* 154: 27-35.
13. Dadachova, E., Mirzadeh, S., Smith, S. V., Knapp, F. F., and Hetherington, E. L. 1997. Radiolabelling antibodies with 166-Holmium. *Appl. Rad. Isotop.* 48: 477-481.
14. Pippin, C. G., Parker, T. A., McMurry, T. J., and Brechbiel, M. W. 1992. Spectrophotometric method for the determination of a bifunctional DTPA ligand in DTPA-monoclonal antibody conjugates. *Bioconjug. Chem.* 3: 342-345.
15. Boll, R. A., Mirzadeh, S., and Kennel, S. J. 1997. Optimizations of radiolabeling of immuno-proteins with 213-Bi. *Radiochim. Acta* 79: 145-149.
16. Mirzadeh, S., Brechbiel, M. W., Atcher, R. W., and Gansow, O. A. 1990. Radiometal labeling of immunoproteins: covalent linkage of 2-(4-isothiocyanatobenzyl) diethylene-triaminepentaacetic acid ligands to immunoglobulin. *Bioconjug. Chem.* 1: 59-65.
17. Dadachova, E., and Mirzadeh, S. 1997. The role of tin in the direct labelling of proteins with rhenium-188. *Nucl. Med. Biol.* 24: 605-608.
18. Feldmesser, M., and Casadevall, A. 1997. Effect of serum IgG$_1$ against murine pulmonary infection with *Cryptococcus neoformans*. *J. Immunol.* 158: 790-799.
19. Rivera, J., Feldmesser, M., Cammer, M., and Casadevall, A. 1998. Organ-dependent variation of capsule thickness in *Cryptococcus neoformans* during experimental murine infection. *Infect. Immun.* 66: 5027-5030.
20. McDevitt, M. R., Barendswaard, E., Ma, D., Lai, L., Curcio, M. J., Sgouros, G., Ballangrud, A. M., Yang, W. H., Finn, R. D., Pellegrini, V. et al 2000. An alpha-particle emitting antibody [213Bi]J591 for radioimmunotherapy of prostate cancer. *Cancer Res.* 60: 6095-6100.
21. Rhodes, J. C., Wicker, L. S. and Urba, W. 1980. Genetic control of susceptibility to *Cryptococcus neoformans* in mice. *Infect. Immun.* 29: 494-499.
22. Mukherjee, J., Zuckier, L. S., Scharff, M. D., and Casadevall, A. 1994. Therapeutic efficacy of monoclonal antibodies to *Cryptococcus neoformans* glucuronoxylomannan alone and in combination with amphotericin B. *Antimicrob. Agents Chemother.* 38: 580-587.
23. Casadevall, A., and Scharff, M. D. 1994. Serum therapy revisited: animal models of infection and development of passive antibody therapy. *Antimicrob. Agents Chemother.* 38: 1695-1702.
24. Behr, T. M., Behe, M., Lohr, M., Sgouros, G., Angerstein, C., Wehrmann, E., Nebendahl, K., Becker, W. 2000. Therapeutic advantages of Auger electron-over beta-emitting radiometals or radioiodine when conjugated to internalizing antibodies. *Eur. J. Nucl. Med.* 27: 753-765.
25. Sharkey, R. M., Blumenthal, R. D., Behr, T. M., Wong, G. Y., Haywood, L. Forman, D., Griffiths, G. L. and Goldenberg, D. M. 1997. Selection of radioimmunoconjugates for the therapy of well-established or micrometastatic colon carcinoma. *Int. J. Cancer* 72: 477-485.
26. Casadevall, A. 1996. Crisis in infectious disease: Time for a new paradigm? *Clin. Infect. Dis.* 23: 790-794.
27. Knapp, F. F. Jr. 1998. Rhenium-188—a generator-derived radioisotope for cancer therapy. *Cancer Biother Radiopharm.* 13: 337-349.
28. Hoher, M., Wohrle, J., Wohlfrom, M., Hanke, H., Voisard, R., Osterhues, H. H., Kochs, M., Reske, S. N., Hombach, V., Kotzerke, J. et al 2000. Intracoronary beta-irradiation with a liquid 188-Re-filled balloon: six-month results from a clinical safety and feasibility study. *Circulation* 101: 2355-2360.
29. Palmedo, H., Guhlke, S., Bender, H., Sartor, J., Schoeneich, G., Risse, J., Grunwald, F., Knapp, F. F. Jr, Biersack, H. J. 2000. Dose escalation study with rhenium-188 hydroxyethylidene diphosphonate in prostate cancer patients with osseous metastases. *Eur. J. Nucl. Med.* 27: 123-130.
30. Kennel, S. J., and Mirzadeh, S. 1998. Vascular targeted radioimmunotherapy with 213-Bi—an alpha-particle emitter. *Nucl. Med. Biol.* 25: 241-246.

31. Behr, T. M., Behe, M., Stabin, M. G., Wehrmann, E., Apostolidis, C., Molinet, R., Strutz, F., Fayyazi, A., Wieland, E., Gratz, S. et al. 1999. High-linear energy transfer (LET) alpha versus low-LET beta emitters in radioimmunotherapy of solid tumors: therapeutic efficacy and dose-limiting toxicity of 213Bi—versus 90Y-labeled CO17-1A Fab' fragments in human colonic cancer model. *Cancer Res.* 59: 2635-2643.

32. Adams, G. P., Shaller, C. S., Horak, E. M., Simmons, H. H., Dadachova, K., Chappell, L. L., Wu, C., Marks, J. D., Brechbiel, M. W. and Weiner, L. M. et al 2000. Radioimmunotherapy of established solid tumor xenografts with alpha and beta emitter-conjugated anti-HER2/neu single-chain Fv (scFv) and diabody molecules. *Cancer Biother. Radiopharm.* 15: 402a. (Abstr.)

33. Kolbert, K. S., Hamacher, K. A., Jurcic, J. G., Scheinberg, D. A., Larson, S. M., Sgouros, G. 2001. Parametric images of antibody pharmacokinetics in 213Bi-HuM195 therapy of leukimia. *J. Nucl. Med.* 42: 27-32.

34. Sgouros, G., Ballangrud, A. M., Jurcic, J. G., McDevitt, M. R., Humm, J. L., Erdi, Y. E., Mehta, B. M., Finn, R. D., Larson, S. M. and Scheinberg, D. A. 1999. Pharmacokinetics and dosimetry of an alpha-particle emitter labeled antibody: 213Bi-HuM195 (anti-CD33) in patients with leukemia. *J. Nucl. Med.* 40: 1935-1946.

35. Goldman, D. L., Casadevall, A., Cho, Y., Lee, S. C. 1996 *Cryptococcus neoformans* meningitis in the rat. *Lab. Invest.* 75: 759-770.

36. Gordon, M. A. and Casadevall, A. 1995. Serum therapy for cryptococcal meningitis. *Clin. Infect. Dis.* 21: 1477-1479.

37. Paganelli, G., Grana, C., Chinol, M., Cremonesi, M., De Cicco, C., De Braud, F., Robertson, C., Zurrida, S., Casadio, C., Zoboli, S. et al 1999. Antibody-guided three-step therapy for high grade glioma with yttrium-90 biotin. *Eur. J. Nucl. Med.* 26: 348-357.

38. Larsen, R. A., Bozzette, S., McCutchan, J. A., Chiu, J., Leal, M. A., Richman, D. D. 1989. Persistent *Cryptococcus neoformans* infection of the prostate after successful treatment of meningitis. California Collaborative Treatment Group. *Ann. Intern. Med.* 111: 125-128.

39. Casadevall, A. and Scharff, M. 1995. Return to the past: the case for antibody-based therapies in infectious diseases. *Clin. Infect. Dis.* 21: 150-161.

40. Goldenberg, D. M. 1995. *Cancer Therapy with Radiolabeled Antibodies*. CRC Press, Boca Raton, Fla.

41. Knox, S. J., and Meredith, R. F. 2000. Clinical radioimmunotherapy. *Semin. Radiat. Oncol.* 10: 73-93.

42. Milenic, D. E. 2000. Radioimmunotherapy: designer molecules to potentiate effective therapy. *Semin. Radiat. Oncol.* 10: 139-155.

43. Buchsbaum, D. J. 2000. Experimental radioimmunotherapy. *Semin. Radiat. Oncol.* 10: 156-167.

44. Becker, W. 1995. The contribution of nuclear medicine to the patient with infection. *Eur. J. Nucl. Med.* 22: 1195-1211.

45. Taborda, C. P. and Casadevall, A. 2001. Immunoglobulin M efficacy against *Cryptococcus neoformans*: mechanism, dose dependence, and prozone-like effect in passive protection experiments. *J. Immunol.* 166: 2100-2107.

46. Krieg, A. M. 2000. Immune effects and mechanisms of action of CpG motifs. Vaccine 19:618-22.

47. Weeratna, R. D., M. J. McCluskie, Y. Xu, and H. L. Davis. 2000. CpG DNA induces stronger immune responses with less toxicity than other adjuvants. Vaccine 18:1755-62.

48. Rosas A L, Nosanchuk J D, Feldmesser M, Cox G M, McDade H C, Casadevall A. Synthesis of polymerized melanin by *Cryptococcus neoformans* in infected rodents. Infect Immun. 2000 68(5): 2845-2853.

49. Lelouard, H., E. Gatti, F. Cappello, O. Gresser, V. Camosseto, and P. Pierre. 2002. Transient aggregation of ubiquitinated proteins during dendritic cell maturation. Nature 517:177-182.

50. Saha G B Fundamentals of Nuclear Pharmacy, Springer, 1997, New York, pp.139-143

51. Paganelli G., Zoboli S., Cremonesi M. et al Receptor-mediated radionuclide therapy with 90-Y-DOTA-D-Phe-Tyr$^3$-Octreotide: Preliminary report in cancer patients. Cancer Biother. Radiopharm. 14: 477-483.

52. Nosanchuk J D, Gomez B L, Youngchim S, Diez S, Aisen P, Zancope-Oliveira R M, Restrepo A, Casadevall A, Hamilton A J. *Histoplasma capsulatum* synthesizes melanin-like pigments in vitro and during mammalian infection. Infect Immun September 2002; 70(9):5124-31.

53. Goldman D L, Casadevall A, Zuckier L S. Pharmacokinetics and biodistribution of a monoclonal antibody to *Cryptococcus neoformans* capsular polysaccharide antigen in a rat model of crypto-coccal meningitis: implications for passive immunotherapy, J. Med. Veterinary Mycol. 1997, 35, 271-278.

54. Schmid A K, Lidstrom M E. Involvement of Two Putative Alternative Sigma Factors in Stress Response of the Radioresistant Bacterium *Deinococcus radiodurans*. J Bacteriol 2002 184(22): 6182-6189.

55. Komarova L N, Petin V G, Tkhabisimova M D Recovery of yeast cells after exposure to ionizing radiation and hyperthermia, Radiation Biology. Radioecology (in Russian), 42, p. 54-59 (2002).

56. Shvedenko V I, Kabakova N M, Petin V G A Comparative study of RBE of densely ionizing radiation for various criteria of yeast cell death, Radiation Biology. Radioecology (in Russian), 41, p. 361-365 (2001).

57. Early P. J. and Sodee D. B. Principles and Practice of Nuclear Medicine, Mosby, 1995.

58. Sayeg J A, Birge A C, Beam C A, Tobias C A. The effects of accelerated carbon nuclei and other radiations on the survival of haploid yeast. II. Biological experiments. *Radiat. Res.* 1959; 10:449-461.

59. Mironenko N V, Alekhina I A, Zhdanova N N, Bulat S A. Intraspecific variation in gamma-radiation resistance and genomic structure in the filamentous fungus *Alternaria alternata*: a case study of strains inhabiting Chernobyl reactor no. 4. *Ecotoxicol. Environ. Saf.* 2000; 45:177-187.

60. Retallack D M and Woods J P. Molecular epidemiology, pathogenesis, and genetics of the dimorphic fungus *Histoplasma capsulatum. Microbes Infect.* 1999; 1:817-825.

61. Nosanchuk J D, Deepe G S, Jr., and Casadevall A. Generation of monoclonal antibodies to *Histoplasma capsulatum* and their effect on murine infection [abstract]. 2001; ASM 101st General Meeting: F-143.

62. Goddu S M, Howell R W, Bouchet L G, Bolch W E, and Rao D V. *MIRD Cellular S values: Self-absorbed dose per unit cumulated activity for selected radionuclides and monoenergetic electron and alpha particle emitters incorporated into different cell compartments*. Society of Nuclear Medicine, Reston, Va., 1997

63. Fantes P and Brooks R. eds. *The Cell Cycle. A Practical Approach*. Oxford University Press, Oxford, UK, 1993.

64. Makrigiorgos G M, Kassis A I, Baranowska-Kortylewicz J. et al. Radiotoxicity of 5-[$^{123}$I]iodo-2'-deoxyuridine in V79 cells: A comparison with 5-[$^{125}$I]iodo-2'-deoxyuridine. *Radiat. Res.* 1989; 118:532-544.

65. Loevinger R, Budinger T F, and Watson E E., *MIRD Primer for Absorbed Dose Calculations*. The Society of Nuclear Medicine, New York, 1991.
66. Pierini L M, Doering T L. Spatial and temporal sequence of capsule construction in *Cryptococcus neoformans*. Mol. Microbiol. 2001; 41:105-115.
67. Murtha A D. Review of low-dose-rate radiobiology for clinicians. Semin. Radiation Oncol. 2000; 10:133-138.
68. Knox S J, Goris M L, Wessels B W. Overview of animal studies comparing radioimmunotherapy with dose equivalent external beam radiation. Radiother. Oncol. 1992; 23:111-117.
69. Xue L Y, Butler N J, Makrigiorgos G M, Adelstein S J, and Kassis A I. Bystander effect produced by radiolabeled tumor cells in vivo. PNAS 2002: 99, 13765-13770.
70. Bishayee A, Rao D V, Howell R W. Evidence for pronounced bystander effects caused by nonuniform distributions of radioactivity using a novel three-dimensional tissue culture model. Radiat Res 1999;152:88-97.
71. Marko N F, Dieffenbach P B, Yan G. et al. Does metabolic radiolabeling stimulate the stress response? Differential cellular responses to internal beta versus external gamma radiation. Faseb J 2003 (August); 17(11) 1470-86.
72. Wentworth P, Jr., McDunn J E, Wentworth A D. et al. Evidence for antibody-catalyzed ozone formation in bacterial killing and inflammation. Science 2002; 298:2195-2199.
73. Appelbaum P C Resistance among *Streptococcus pneumoniae*: implications for drug selection, Clin. Infect. 34: 1613-1620, 2002.
74. Pirofski L -A, Casadevall A. 1998 The use of licensed vaccines for active immunization of the immunocompromised host. Clin. Microbiol. Rev. 11: 1-26.
75. Chappell L L, Dadachova E, Milenic D E, Garmestani K, Brechbiel M W. Synthesis and Characterization of a Novel Bifunctional Chelating Agent for Lead(II). Conjugation to a Monoclonal Antibody, Radiolabeling with Lead-203 and Serum Stability Determination, Nucl. Med. Biol. 27: 93-100, 2000
76. Miale, J. B. (1982) *Laboratory Medicine Hematology* (The CV Mosby Company, St. Louis), p. 864.
77. Zhong Z, Burns T, Chang Q, Carroll M, Pirofski L. Molecular and functional characteristics of a protective human monoclonal antibody to serotype 8 Streptococcus pneumoniae capsular polysaccharide. Infect Immun. August 1999; 67(8):4119-27.
78. Abbas A K, Lichtman A H, Pober J S. Cellular and Molecular Immunology, 4th edition, W. B. Saunders Co., Philadelphia, 2000.
79. Dadachova E., Nakouzi A., Bryan R., and Casadevall A. Ionizing radiation delivered by specific antibody is therapeutic against a fungal infection, Proc Natl Acad Sci USA. 100 (19): 10942-10947 (Sep. 16, 2003)
80. Dadachova E., Howell R. W., Bryan R. A., Frenkel A., Nosanchuk J. D., Casadevall A. Susceptibility of human pathogens *Cryptococcus neoformans* and *Histoplasma capsulatum* to gamma radiation versus radioimmunotherapy with alpha- and beta-emitting radioisotopes, J. Nucl. Med., in print
81. Nosanchuk J D, Valadon P, Feldmesser M, Casadevall A. Melanization of *Cryptococcus neoformans* in murine infection. Mol Cell Biol. 19: 745-750, 1999.
82. Valadon, P., G. Nussbaum, L. F. Boyd, D. H. Margulies, and M. D. Scharff. Peptide libraries define the fine specificity of anti-polysaccharide antibodies to *Cryptococcus neoformans*. J. Mol. Biol. 261:11-22, 1996.
83. Fleuridor R, Lees A, and Pirofski L. A cryptococcal capsular polysaccharide mimotope prolongs the survival of mice with *Cryptococcus neoformans* infection. J Immunol 166:1087-1096, 2001.
84. Sivanathan S, Duncan J L, Urquhart G M. Some factors influencing the immunisation of sheep with irradiated Haemonchus contortus larvae. Vet. Parasitol. 1984, 16(3-4): 313-23.
85. Hernigou P, Gras G, Marinello G, Dormont D. Inactivation of HIV by application of heat and radiation: implication in bone banking with irradiated allograft bone. Acta Orthop Scand. 2000; 71(5):508-12.

What is claimed is:

1. A method for treating a fungal infection in a subject which comprises administering to a subject having a fungal infection a monoclonal antibody labeled with a beta-emitting radioisotope in an amount effective to reduce fungal levels in the subject, wherein the monoclonal antibody specifically binds to the fungus causing the infection, wherein the anti-fungal monoclonal antibody is labeled with the beta-emitting radioisotope prior to administering the antibody or the beta-emitting radioisotope to the subject, and wherein the anti-fungal monoclonal antibody labeled with the beta-emitting radioisotope is administered to the subject in an amount and manner effective to reduce fungal levels in the subject's brain.

2. The method of claim 1 wherein the subject is immunosuppressed.

3. The method of claim 1, wherein the fungal infection is caused by a fungus selected from the group consisting of *Cryptococcus neoforman, Histoplasma capsulatum* and *Aspergillus fumigatus*.

4. The method of claim 1, wherein the fungal infection is caused by *Cryptococcus neoforman*.

5. The method of claim 1, wherein the antibody is an IgG1 antibody or an IgM antibody.

6. The method of claim 1, wherein the beta-emitting radioisotope is 188-Rhenium.

7. The method of claim 1, wherein the infection is located within an abscess within the subject.

8. The method of claim 1 where the subject is a mammal.

9. The method of claim 8 wherein the mammal is a human.

10. The method of claim 9 wherein the antibody labeled with the beta-emitting radioisotope is administered at a dose of radioisotope between 1-500 milliCuries.

11. The method of claim 1, wherein the antibody is directly labeled with the beta-emitting radioisotope prior to administering the antibody to the subject.

12. The method of claim 1, wherein the antibody is labeled with the beta-emitting radioisotope via reduction of antibody disulfide bonds prior to administering the antibody to the subject.

13. The method of claim 1, wherein the antibody is labeled with the beta-emitting radioisotope via a bifunctional chelating agent prior to administering the antibody to the subject.

14. The method of claim 1, wherein treatment of the fungal infection with the antibody labeled with the beta-emitting radioisotope reduces the fungal infection so that the fungal infection is amenable to the subject's immune defenses.

15. The method of claim 1, further comprising the step of administering the anti-fungal monoclonal antibody labeled with the beta-emitting radioisotope is to the subject in an amount and manner effective to reduce fungal levels in the lungs of the subject.

16. The method of claim 1, wherein the anti-fungal monoclonal antibody labeled with the beta-emitting radioisotope is administered to the subject in an amount effective to prolong survival of the subject.

17. The method of claim 1, wherein the fungal infection is treated in a subject who is a cancer patient.

18. The method of claim 1, wherein the fungal infection is treated in a subject who is an organ transplant recipient.

19. The method of claim 1, wherein the fungal infection is treated in a subject who has human immunodeficiency virus (HIV).

* * * * *